United States Patent [19]
Yashida et al.

[11] Patent Number: 5,365,564
[45] Date of Patent: Nov. 15, 1994

[54] METHOD AND APPARATUS FOR BONE MORPHOMETRY AND A MORPHOMETRIC BONE ASSAY SYSTEM

[75] Inventors: Makoto Yashida, Kobe; Kanji Kurome, Ibaragi; Atsushi Asahina, Ibaragi; Yasuki Hanaoka, Ibaragi; Kazuo Imose, Takarazuka, all of Japan

[73] Assignee: Teijin Limited, Osaka, Japan

[21] Appl. No.: 601,716

[22] PCT Filed: Feb. 23, 1990

[86] PCT No.: PCT/JP90/00220
§ 371 Date: Oct. 23, 1991
§ 102(e) Date: Oct. 23, 1991

[87] PCT Pub. No.: WO90/09761
PCT Pub. Date: Sep. 7, 1990

[30] Foreign Application Priority Data

Feb. 23, 1989 [JP] Japan .................. 1-41760
May 16, 1989 [JP] Japan .................. 1-120376
May 31, 1989 [JP] Japan .................. 1-136176

[51] Int. Cl.⁵ ............................. G01N 23/06
[52] U.S. Cl. ......................... 378/55; 378/56
[58] Field of Search ............. 378/54, 55, 56, 62, 378/901; 364/413.01, 413.02, 413.13, 413.14

[56] References Cited

U.S. PATENT DOCUMENTS

| | | | |
|---|---|---|---|
| 3,639,764 | 2/1972 | Olson et al. | 250/83.3 D |
| 4,383,327 | 5/1983 | Kruger | 378/19 |
| 4,563,701 | 1/1986 | Gilath et al. | 358/111 |
| 4,721,112 | 1/1988 | Hirano et al. | 128/659 |
| 4,764,870 | 8/1988 | Haskin | 364/415 |
| 4,811,373 | 3/1989 | Stein | 378/54 |
| 4,903,203 | 2/1990 | Yamashita et al. | 364/413.15 |

FOREIGN PATENT DOCUMENTS

| | | |
|---|---|---|
| 61-109557 | 5/1986 | Japan . |
| 62-112538 | 5/1987 | Japan . |
| 0291551 | 12/1987 | Japan .................. 378/54 |

OTHER PUBLICATIONS

K.-A. Omnell, *Acta Radiologica*, Supplement 148, 1957, p. 54.
Kotsu Taisha, vol. 14, pp. 187-195, 1980.
Kotsu Taisha, vol. 14, pp. 91-104, 1981.
English Counterpart of Kotsu Taisha, vol. 14, pp. 91-104, 1981.

*Primary Examiner*—Paul M. Dzierzynski
*Assistant Examiner*—David V. Bruce
*Attorney, Agent, or Firm*—Sughrue, Mion, Zinn, Macpeak & Seas

[57] ABSTRACT

A bone-morphometric apparatus (20) is provided with a bone-morphometric data processing unit (32), including at least an image storage unit, such as an image memory (56), a microprocessor unit (60), and an input unit for entering reference points to specify an object measuring region. The data processing unit (32) stores either digital data of an X-ray image (22a) of a sample bone formed on an X-ray film (22) simultaneously with an image of a given standard block (11), obtained by illuminating the X-ray film with illuminating light from a light source (41) and automatically detecting the quantity of light transmitted through the image (22a) by an image detector (42), or digital data of a radiographic image of the sample bone obtained by a radiographic image-forming apparatus (90) in the image storage unit, so as to subject the stored digital data to arithmetic operation, to thereby obtain bone-morphometric data. At least one bone-morphometric apparatus (20) may be connected to a morphometric bone assay apparatus (351) by means of a communications means (350), in order to constitute a morphometric bone assay system.

36 Claims, 20 Drawing Sheets

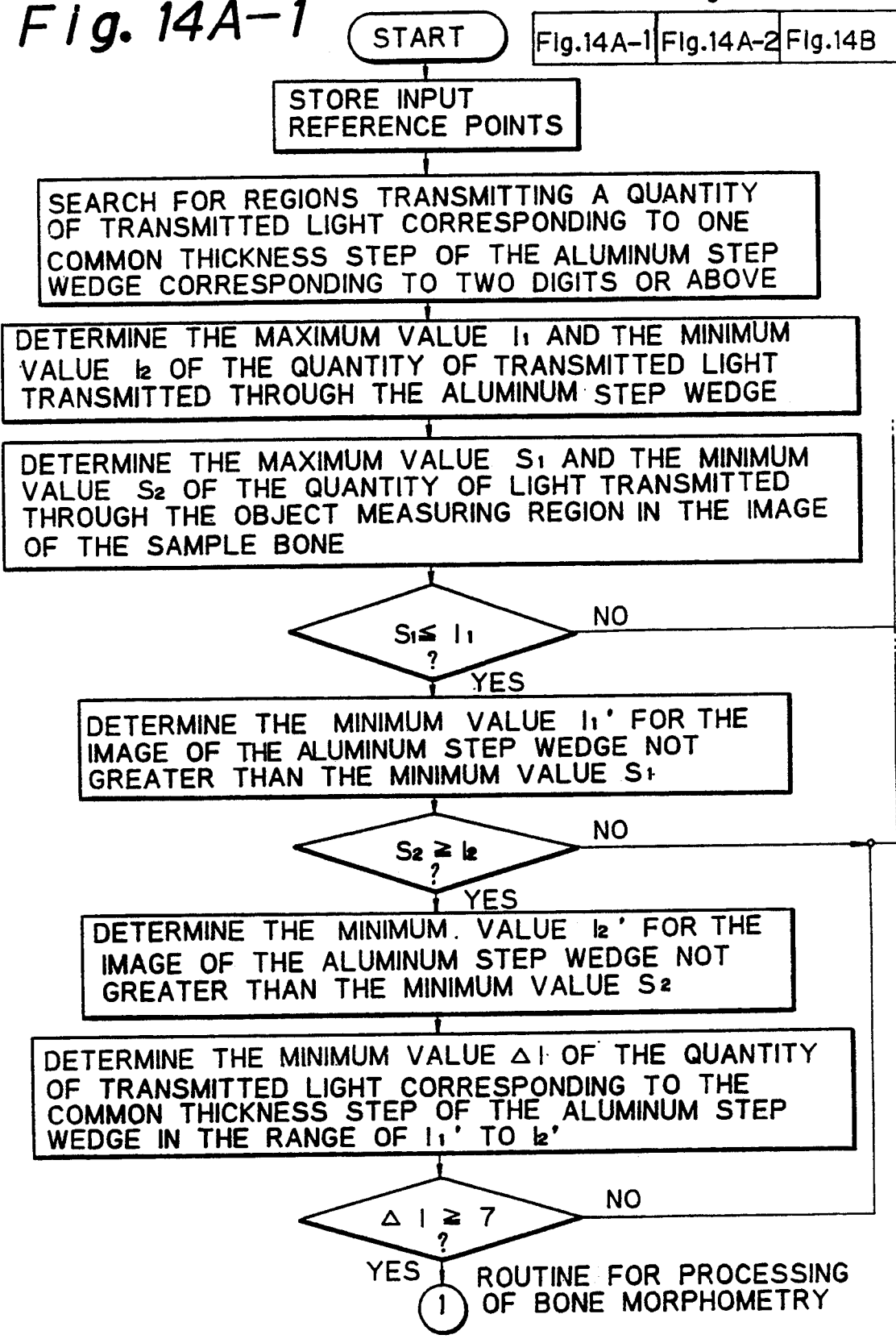

METHOD AND APPARATUS FOR BONE MORPHOMETRY AND A MORPHOMETRIC BONE ASSAY SYSTEM

TECHNICAL FIELD

The present invention relates to an automated bone morphometry and morphometric bone assay, and more specifically, to an automatic bone morphometry method using radiographs or roentgenograms and a bone-morphometric apparatus for carrying out the method, and a morphometric bone assay system connected with the bone-morphometric apparatus by a communication system and capable of efficiently carrying out a morphometric bone assay and bone history assay.

BACKGROUND ART

Bone morphometry is applied to the confirmation of the growth and aging of human bones, the diagnosis and confirmation of the rate of progress of bone diseases including osteoporosis and osteomalacia, and the confirmation of the effect of treatment.

Microdensitometry (MD), photon-absorptiometry and radioscopy are generally known bone morphometric methods. Microdensitometry (Kotsu Taisha, Vol. 13, pp. 187-195 (1980); Kotsu Taisha, Vol. 14, pp. 91-104 (1981)) measures the tone of the roentgenogram of a sample bone by a microdensitometer for bone morphometry; photon absorptiometry measures the quantity of gamma rays transmitted through a sample bone by a detector for bone morphometry; and radioscopy measures the quantity of X-rays transmitted through a sample bone by a detector for bone morphometry. A morphometric bone assay method disclosed in U.S. Pat. No. 4,721,112 assays bones on the basis of bone density distribution determined by measuring roentgenographic bone patterns.

Microdensitometry has become increasingly widely used because the method uses readily available roentgenograms which can be easily obtained by an X-ray camera used widely for diagnosing bone fractures. Photon absorptiometry has a drawback in that use of the gamma-ray generator has not become as wide-spread as that of the X-ray camera.

The conventional microdensitometric bone morphometry, however, requires many steps of manual work. When carrying out the conventional microdensitometric bone morphometry, a reference point for bone morphometry is determined in the roentgenographic bone image of a sample bone, an object measuring region, such as a region on a line crossing the middle point of the longitudinal axis of the second metacarpal bone, is selected by a predetermined procedure with reference to the reference point, the selected region is scanned by a microdensitometer, the intensity or quantity, preferably quantity, of light transmitted through the region is measured, and the measured quantity of light transmitted through the region or the measured quantity of light absorbed by the region is recorded as a diagram on a chart. On the other hand, the roentgenogram of an aluminum standard step block, namely, an aluminum step wedge or an aluminum slope, taken together with the roentgenogram of the sample bone is scanned along its longitudinal axis by the microdensitometer, and the measured quantity of light transmitted through or absorbed by the aluminum standard step block is recorded as a diagram on a chart. Then the diagram of the quantity of absorbed light is converted into digital data by a digitizer, the digital data is applied to an electronic computer to convert the quantities of absorbed light at points on the sample bone into corresponding gradations of the aluminum standard step block, and the computer calculates various indices representing the bone-morphology of the region on the basis of a pattern expressed by the gradations of the aluminum standard step block.

Thus, the conventional microdensitometry requires manual work for the selection of the object measuring region in the roentgenogram of the bone, which is troublesome and time-consuming. The light absorption diagram must be scanned by manually operating the digitizer to give the computer the digital data, which is an obstacle to an accurate, quick measurement of the bone. When many sample bones must be measured and many roentgenograms must be analyzed, in particular, the conventional microdensitometry requires much time and labor, which is disadvantageous from an economic viewpoint as well as from that of the rapidity of a measurement.

The tone of the roentgenographic image of the sample bone is greatly dependent on the X-ray condition and developing condition, and the measurement of the roentgenogram is impossible or, even if the roentgenogram can be measured, the measured result includes large errors.

Furthermore, the bone-morphometric examination cannot be performed immediately after the X-ray, because the roentgenogram must be transported from the X-ray place to the roentgenogram examining place far from the X-ray place. Moreover, the installation of both an X-ray apparatus and a bone-morphometric apparatus at the same place requires a morphometric bone assay apparatus in combination with each bone-morphometric apparatus, which increases the cost of the system and labor for the maintenance of the system, and thus is economically disadvantageous.

DISCLOSURE OF THE INVENTION

Accordingly, the first object of the present invention is to solve the problems of the conventional bone morphometry.

A second object of the present invention is to provide a method and an apparatus for bone morphometry, capable of automatically and accurately carrying out a bone-morphometric operation.

A third object of the present invention is to provide a method and an apparatus for bone morphometry, capable of automatically reading the roentgenogram of a sample bone to obtain bone-morphometric data, quickly analyzing the bone-morphometric data, and properly correcting the bone-morphometric data.

A fourth object of the present invention is to provide an improved bone-morphometric apparatus capable of efficiently reading only a specified region in the roentgenogram of a sample bone, when automatically reading the roentgenographic image of the sample bone to obtain bone-morphometric data.

A fifth object of the present invention is to provide a method and an apparatus for bone morphometry, capable of adjusting the intensity of light for illuminating the roentgenogram of a sample bone to obtain bone-morphometric data according to the condition of the roentgenogram.

A sixth object of the present invention is to provide a method and an apparatus for bone morphometry, capable of automatically and accurately reading the roentgenographic image of an aluminum standard step block, i.e., an aluminum standard step wedge, when reading a roentgenogram having the respective roentgenographic images of a sample bone and the aluminum standard step block to obtain bone-morphometric data.

A seventh object of the present invention is to provide a method and an apparatus for automated bone morphometry, capable of displaying the bone-morphometric data of a sample bone as a picture, specifying a point or a mark indicating a morphometric reference position on the picture, and erasing the point or the mark.

An eighth object of the present invention is to provide a bone-morphometric apparatus capable of carrying out a more rational bone-morphometric operation than the conventional bone-morphometric apparatus for morphometric bone assay, based on the analysis of the bone density represented by data obtained by efficiently reading the roentgenographic image of a sample bone.

A ninth object of the present invention is to provide a morphometric bone assay system connected to a plurality of bone-morphometric apparatuses by communication lines and capable of receiving bone-morphometric data from the plurality of bone-morphometric apparatuses and sending back bone-morphometric data including the history of the sample bones to the bone-morphometric apparatuses.

In a first aspect of the present invention, a bone-morphometric apparatus comprises, in combination: an automatic image read unit for reading the data of the roentgenographic image of a sample bone through a measurement of light transmitted through a roentgenogram having the respective roentgenographic images of the sample bone and a given standard matter; an image memory unit for storing roentgenographic image data of the sample bone obtained by the automatic image read unit; an arithmetic unit which processes the roentgenographic image data for bone morphometry; and bone-morphometric data output unit which provides bone-morphometric data obtained through the operation of the arithmetic unit.

Preferably, the bone-morphometric apparatus further comprises picture display means for displaying a picture of the image of the sample bone represented by the image data of the sample bone obtained by the automatic image read unit, and point input for giving a point input representing a reference position in the picture of the sample bone displayed by the picture display means necessary for bone morphometry.

In a second aspect of the present invention, a morphometric bone assay system comprises a bone-morphometric apparatus for measuring the morphology of a sample bone, a first transmission unit for sending out bone-morphometric data obtained by the bone-morphometric apparatus, a morphometric bone assay unit for storing the bone-morphometric data and for assaying the sample bone by using the bone-morphometric data, previously obtained bone-morphometric data corresponding to the bone-morphometric data and, if necessary, other stored data, and a second transmission unit for transmitting the results of the morphometric bone assay to the bone-morphometric apparatus.

In a third aspect of the present invention, a bone-morphometric method, which uses the quantity of transmitted light measured by illuminating a roentgenogram having the roentgenographic image of the sample bone and that of a given standard matter having a gradational thickness and X-rayed together with the sample bone for the measurement of the sample bone, comprises: selecting a region of the roentgenographic image of the standard matter, the quantity of light transmitted through the region meeting predetermined conditions, making a first decision to see if the quantity of light transmitted through a measured portion is within the range of the quantity of light transmitted through the standard matter, making a second decision to see if the quantity of light transmitted through the measured portion and the corresponding quantity of light transmitted through the standard matter meet a predetermined resolution, and adjusting the quantity of light for illuminating the roentgenogram on the bases of the result of the second decision.

In a fourth aspect of the present invention, a bone-morphometric method comprises a reading step of reading a transmitted radiographic image obtained by exposing a sample bone to radioactive rays, a smoothing step of obtaining a first smoothed pattern by obtaining the density pattern of the sample bone along a plurality of substantially parallel scanning lines in the vicinity of an object portion of the transmitted radiographic image and smoothing the density pattern at the corresponding positions, a pattern converting step of converting the smoothed density pattern into a thickness pattern represented by the thickness of the standard matter, and an operating step of processing the thickness pattern for bone morphometry.

When necessary, the bone-morphometric method may comprise a step of obtaining a second smoothed pattern by smoothing the data of a plurality of points in areas extending along the measuring lines.

In a fifth aspect of the present invention, a bone-morphometric method, which uses the quantity of transmitted light measured by illuminating a roentgenogram having the roentgenographic image of a sample bone and that of a given standard matter having a gradational thickness and X-rayed together with the sample bone for measuring the sample bone, comprises: a detecting step of detecting one end of the roentgenographic image of the standard matter corresponding to the thicker end of the standard matter by applying a predetermined small quantity $L_0$ of light to a region around the end of the roentgenographic image of the standard matter and measuring the quantity of light transmitted through the region, and determining the relationship between the gradational thickness of the standard matter and the gradation of the roentgenographic image of the standard matter from the relationship between the quantity of transmitted light measured by applying a quantity L of light greater than the quantity $L_0$ to the roentgenographic image of the standard matter and the distance from the end of the roentgenographic image corresponding to the thicker end of the standard matter.

BRIEF DESCRIPTION OF THE DRAWINGS

The above and other objects, features and advantages of the present invention will become more apparent from the following description taken in connection with the accompanying drawings, in which:

FIGS. 14A, 14A-2 and 14B are flow charts of a process of correcting the quantity of illuminating light to be executed by a microprocessor when automatically reading the roentgenographic images of a sample bone and an aluminum standard step wedge;

BEST MODE OF CARRYING OUT THE INVENTION

The bone morphometry in accordance with the present invention uses a radiographic image obtained by exposing a sample bone to radioactive rays, such as gamma rays or X-rays, or a roentgenographic image of a sample bone obtained by an X-ray of the sample bone together with a standard step block. The roentgenographic image formed on an X-ray film, principally, represents the tone and shape of the image of the sample bone formed on the X-ray film. Usually, the standard step block is an aluminum step wedge. A tapered aluminum rod or block (aluminum slope) may be used instead of the aluminum step wedge. A bone which forms a high-contrast roentgenogram, such as a bone having a uniform, thin layer of soft tissues, is desirable. Desirable bones are bones of the hand, and long bones, such as humerus, radius, ulna femur and tibias. The second metacarpal bone is practically most desirable. Cancellous bones, such as calcaneus, vertebra and epiphyses of long bones may be used as sample bones. The calcaneus is practically most desirable.

Figure 2:
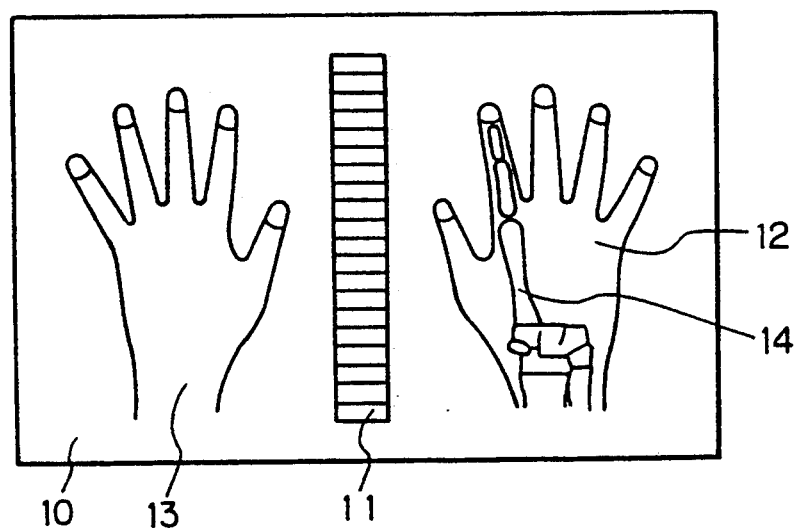
FIG. 2 is a plan view illustrating the arrangement of objects, namely, a sample bone and an aluminum standard step wedge, i.e., a standard step block, for X-ray.

FIG. 2 shows an arrangement of sample bones, i.e., bones of the hand, and an aluminum step wedge on a taking plane for an X-ray. In FIG. 2, the right hand 12, the left hand 13 and an aluminum step wedge 11 are placed on an X-ray dry plate 10, and the second metacarpal bone 14 of the right hand 12 is shown.

Figure 1:
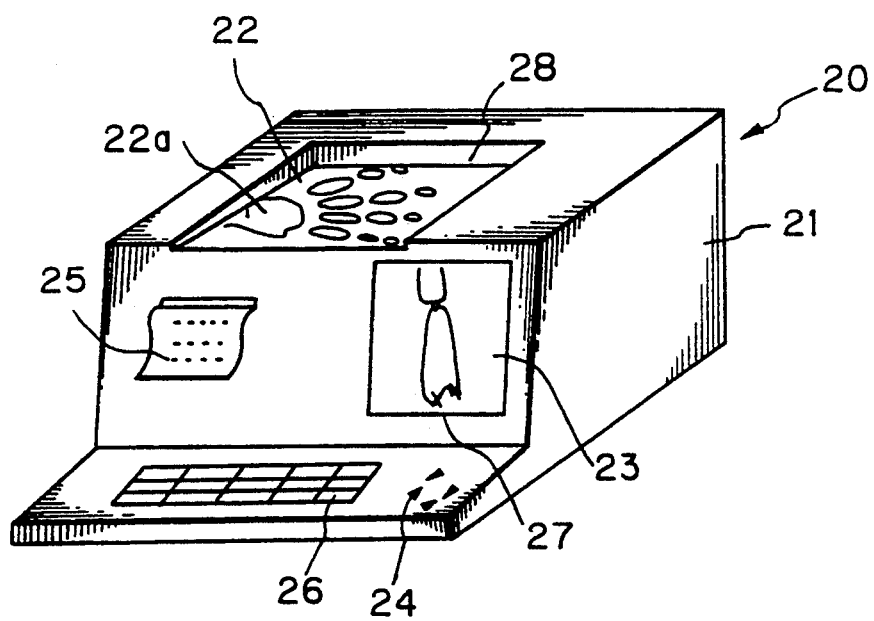
FIG. 1 is a perspective view of a bone-morphometric apparatus in a preferred embodiment according to the present invention.

Referring now to FIG. 1, an X-ray bone-morphometric apparatus 20 embodying the present invention has a boxed-shaped case 21 provided in its upper wall with a film feed table 28 for supporting an X-ray film 22 having an image 22a of the sample bone (the image of the aluminum step wedge is omitted). Arranged in the front portion of the case 21 are display unit 23 for displaying a picture corresponding to the images formed on the X-ray film, a point input unit 24 having, for example, push-button switch means for moving and locating a cursor, not shown, in the screen of the display unit 23 to give a point 27 indicating a reference position, an output unit 25 for printing out the results of bone morphometry, for example, on a paper sheet, and an input unit 26 provided with means, for example, a keyboard, for giving control commands for controlling various operations.

Figure 3:
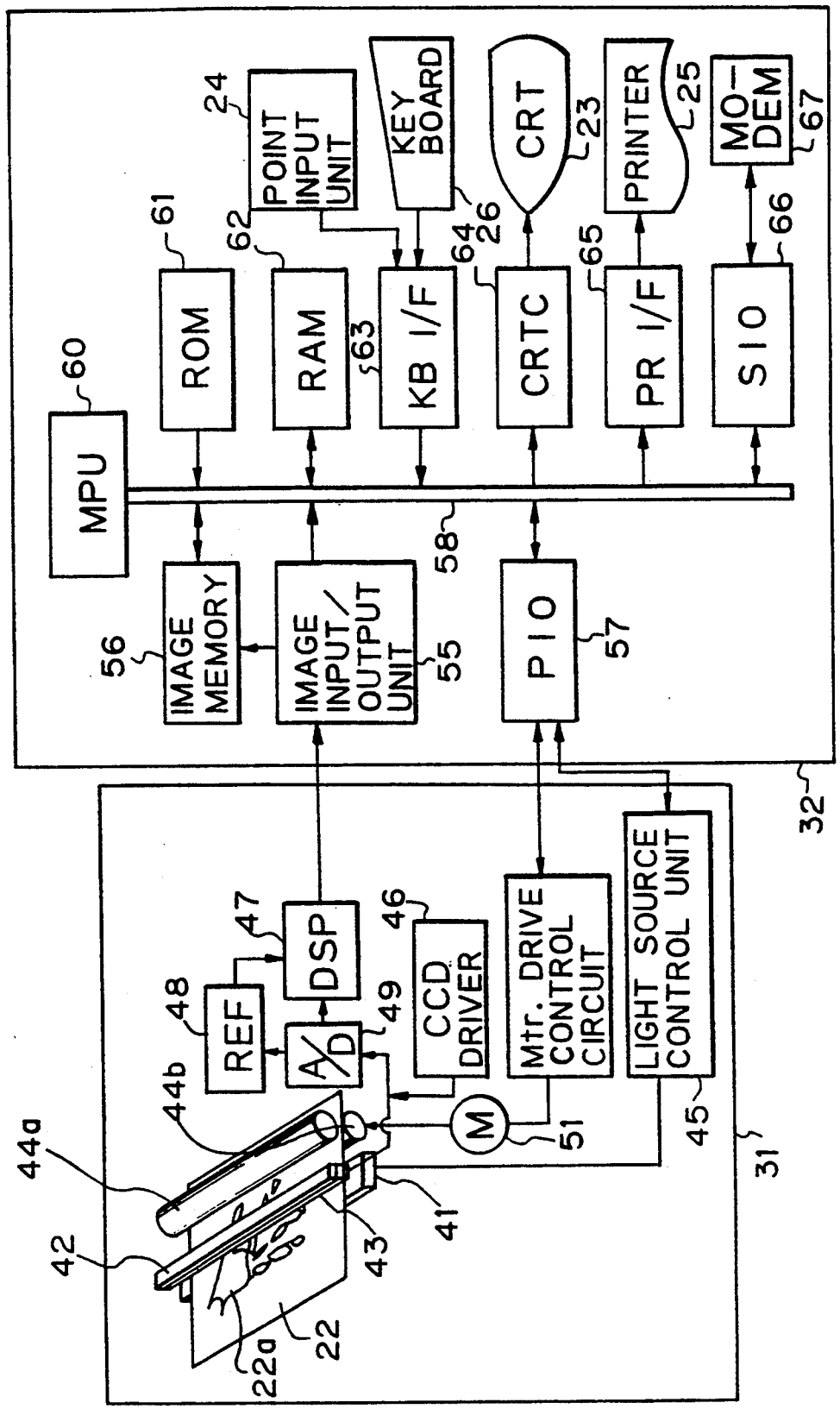
FIG. 3 is a block diagram of the functional configuration of the bone-morphometric apparatus of FIG. 1 including an internal bone-morphometric data processing unit.

Referring to FIG. 3, the bone-morphometric apparatus 20 shown in FIG. 1 comprises morphometric functional units including the foregoing units, an automatic image read unit 31, and a bone-morphometric data processing unit 32 for recording and analyzing an image read by the automatic image read unit 31.

The automatic image read unit 31 comprises a light source 41 for illuminating the X-ray film 22 having the image 22a of the sample bones, i.e., the bones of the right hand, an image detector 42 for detecting transmitted light combined with a focusing lens 43 to detect the quantity of light transmitted through the X-ray film 22 when the X-ray film 22 is illuminated by the light emitted by the light source 41, and an automatic film feed means, which will be described afterward, for feeding the X-ray film 22 in a predetermined direction F.

The light source 41 may be a point light source which emits a light beam which falls on a surface as a spot. Since the point light source requires a scanning mechanism to move the point light source along the surface of the X-ray film 22 for scanning, preferably the light source 41 is a linear light source, such as a linear LED (light emitting diode), a high-frequency-lighting tubular fluorescent lamp, a dc-lighting tubular lamp, or a linear light source formed by bundling optical fibers with their ends arranged in a line and provided with a lamp for emitting light toward the other ends of the optical fibers. The light source 41, such as a linear LED, is extended widthwise of the X-ray film 22. A light source control circuit 45 turns the light source 41 on and off and adjusts the quantity of illuminating light emitted by the light source 41.

Figure 6:
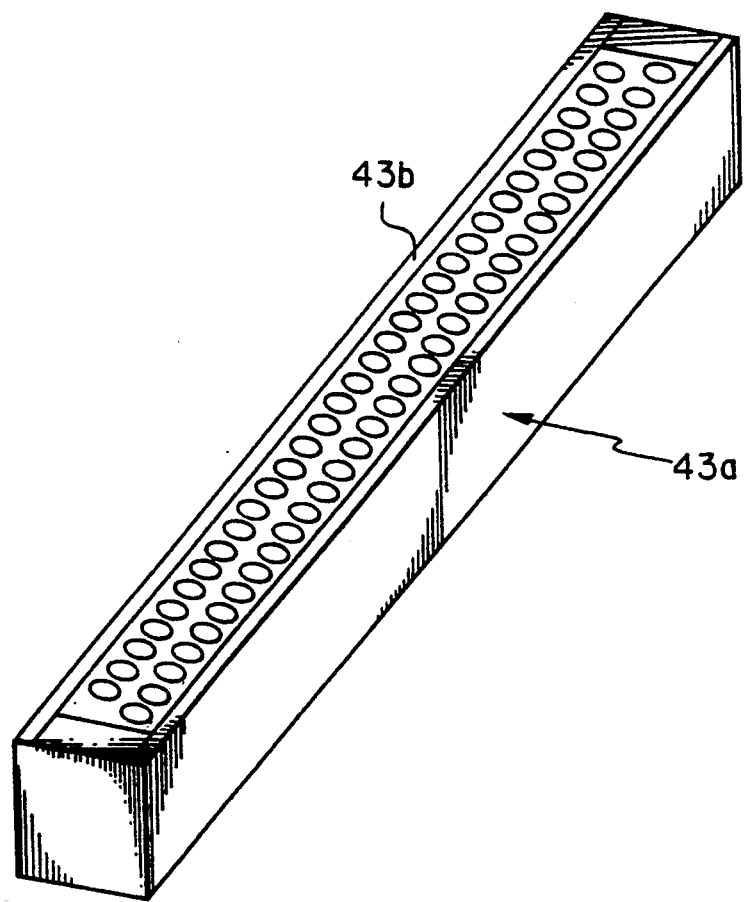
FIG. 6 is a perspective view of an example of a focusing rod lens.

The image detector 42 may be of any type capable of detecting transmitted light for the automatic reading of the image 22a. When used in combination with the linear light source 41, the image detector 42 is a linear image detector. The practically preferable linear image detector is a contact linear image detector formed by linearly arranging, for example, CCDs (charge-coupled devices). To enable a roentgenographic tone measurement with a spatial resolution not lower than that of the microdensitometer, namely, 40% MTF (modulation transfer function) and 1.7 to 1.9 lines per millimeter, such a contact, linear image detector is formed by linearly arranging 4096 CCDs at a pitch of 65 $\mu$m in a direction substantially perpendicular to the X-ray film feed direction F. Light emitted by the linear light source (LED) 41 and transmitted through the X-ray film 22 is focused by the focusing lens 43 on the image detector 42. Then, the image detector 42 provides signals representing the tone of the image formed on the X-ray film 22. The X-ray film 22 may be fed stepwise at a minute feed step of 65 $\mu$m by a driving motor 51, such as a stepping motor. The CCDs of the linear image detector 42 are, preferably, capable of providing an analog voltage signal proportional to the incident light quantity, namely, the quantity of light corresponding to the density of the image formed on the X-ray film 22. A rod lens 43a as shown in FIG. 6 is used preferably as the focusing lens 43. Preferably, the rod lens 43a is constructed by placing two rows each of a linear arrangement of about 250 refractive index profile lenses formed by bundling and resin-bonding a plurality of short optical fibers arranged along a direction perpendicular to their axes in a case 43b. The detecting action of the image detector 42 comprising CCDs is controlled by a CCD driver 46 so that data accumulated in the CCDs can be read according to given timing. Since the respective component elements of the linear light source 41, the linear image detector 42, and the focusing lens 43 comprising the rod lens 43a are arranged linearly widthwise of the X-ray film 22, the characteristics thereof vary with respect to the width of the X-ray film 22. The automatic image read unit 31 is provided with a DSP (digital signal processor) 47, a REF memory (reference data memory) 48 and an A/D converter (analog-to-digital converter) 49 to correct variations in the characteristics of the linear light source 41, the linear image detector 42 and the focusing lens 43. Preferably, the resolution of the A/D converter 49 is eight bits (256) or higher so that the resolution of the A/D converter 49 is not lower than that of the microdensitometer. The time-dependent variation in the performance of the automatic image read unit 31 attributable to the deterioration of the linear light source 41, dust accumulation on the rod lens 43a and the change of the sensitivity of the linear image detector 42 can be automatically compensated by the DSP 47, the REF memory 48 and the A/D converter 49.

The automatic film feed means for feeding the X-ray film 22 comprises a pair of feed rollers 44a and 44b, a driving motor 51 for driving one of the feed rollers 44a and 44b, for example, the feed roller 44b, and a motor driver/controller 52. The X-ray film 22 may be fed either continuously or intermittently, and thus the driving motor 51 may be a stepping motor, a dc motor or an ac motor. Since it is desirable to feed the X-ray film 22 in the direction F perpendicular to the direction of extension of the linear image detector 42 for the detection of the transmitted light by the linear image detector 42, it is preferable to feed the X-ray film 22 intermittently at a minute step in the range of 65 to 100 $\mu$m for image detection in a higher accuracy by the linear image detector 42 comprising CCDs. Therefore, the driving motor 51 is preferably a stepping motor, the stepping operation of which can be easily controlled by a pulse signal.

The accuracy of detection of the image detector 42 and the film feed speed can be enhanced by synchronously controlling the light source 41 and the automatic film feed means so that the light source 41 is turned on only while the X-ray film 22 is stopped through the cooperative operation of the light source controller 45 and the motor driver/controller 52. The light source controller 45 is also capable of adjusting the quantity of illuminating light emitted by the light source 41 according to the density level of the image formed on the X-ray film 22. That is, when a low-contrast image is formed on the X-ray film 22 and the difference between the output signals of the image detector 42 respectively representing the densities at different positions in the image is small, the measuring sensitivity is not sufficiently high. Accordingly, the quantity of light emitted by the light source 41 is adjusted so that the quantities of light transmitted through portions of the image of the aluminum step wedge 11 (FIG. 2) corresponding to the stepped sections of the aluminum step wedge 11 meet predetermined conditions.

It is also possible to specify a narrow region containing an object part in the image 22a, to automatically read only a portion of the image 22a corresponding to the object part.

The operation of the correcting means of the automatic image read unit 31, comprising the DSP 47, the REF memory 48 and the A/D converter 49 will be described hereinafter. Prior to mounting the X-ray film 22 on the automatic image read unit 31, light is projected by the linear light source 41 directly on the linear image detector 42 through the focusing lens 43, i.e., the rod lens 43a, and the quantity of light emitted by the linear light source 41 is adjusted so that the respective maximum analog outputs of the components of the linear image detector 42 are not saturated and are nearly equal to the upper limit of the scale. Then, the light-quantity detection pattern of the image detector 42 is converted into digital data by the AD converter 49 and the digital data is stored in the REF memory 48 as reference data for the components of the linear image detector 41. Subsequently, the X-ray film 22 is subject to bone morphometry on the automatic image read unit 31. A light-quantity detection pattern obtained by detecting the quantities of transmitted light transmitted through parts of the X-ray film 22 corresponding to the elements of the linear image detector 41 (data obtained by the elements of the linear image detector 41 will be designated as "MES data") is corrected by the DSP 47 by a procedure expressed by Expression (1), $$\{(MES\ data/REF\ data)\} \times (Maximum\ REF\ data) = Corrected\ data \qquad (1)$$

and then the DSP 47 provides the corrected data as the image data of the image 22a formed on the X-ray film 22.

Figure 7A:
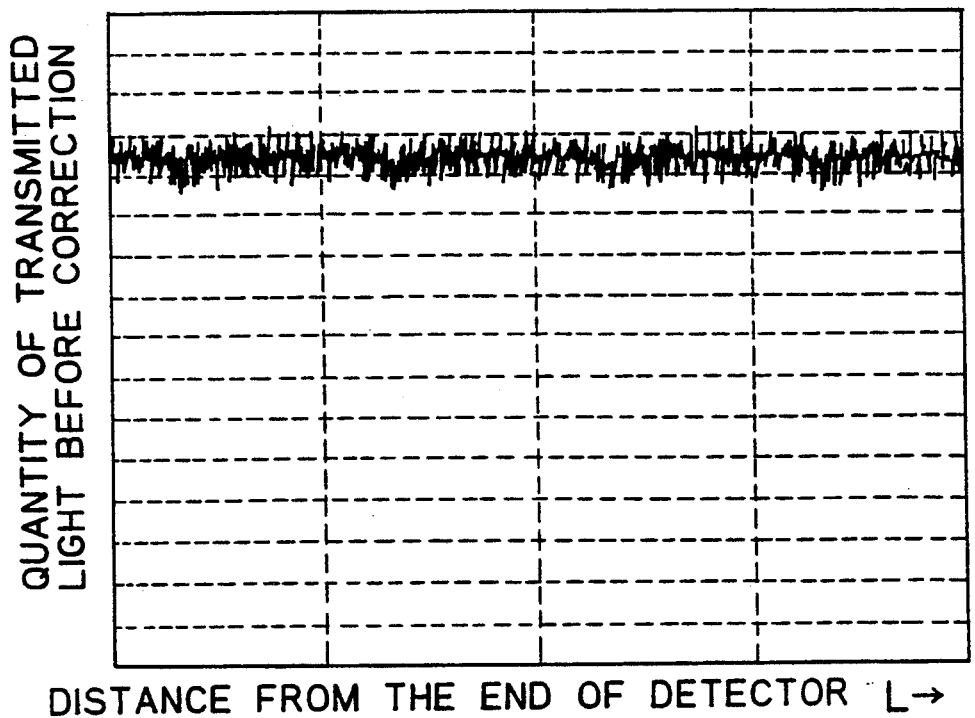
FIGS. 7A and 7B are graphical views of assistance in explaining the effect of a linear detector on the correction of detected values.
Figure 7B:
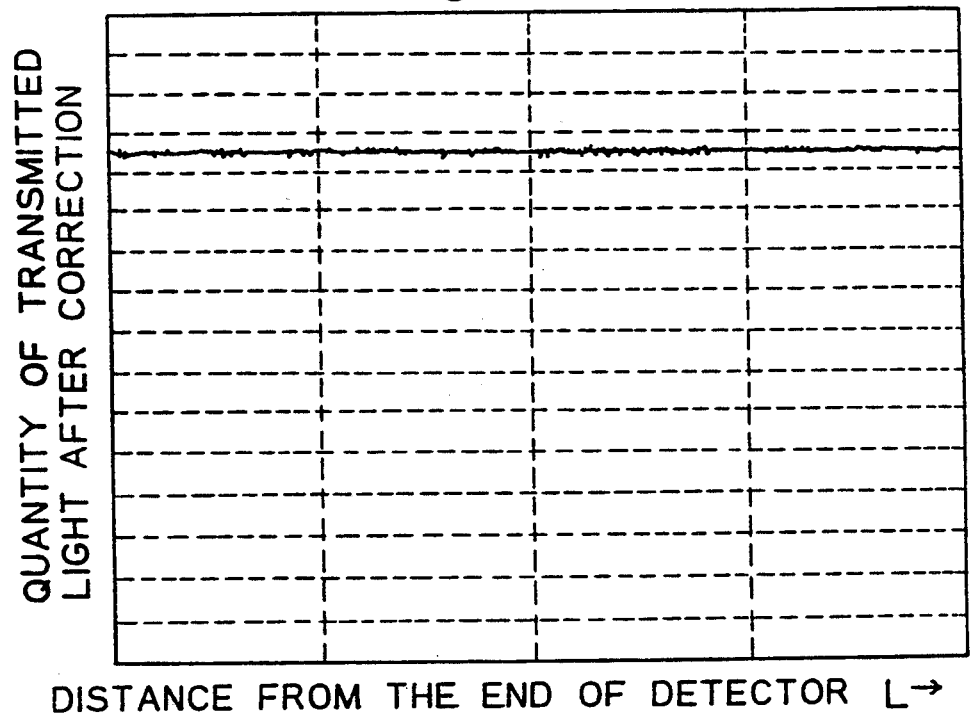

FIGS. 7A and 7B are the results of experiment conducted to confirm the effect of correction. FIG. 7A shows the light-quantity detection pattern obtained by directly illuminating the linear light source 41 without placing the X-ray film between the linear light source 41 and the linear image detector 42, and FIG. 7b shows the corrected light-quantity detection pattern, which proves the effective correction of variations in the light-quantity detection pattern of FIG. 7A.

It is preferable to perform the correcting operation every time the transmitted light is detected after feeding the X-ray film 22 by the minute distance to eliminate the need for a special time for correction.

When an object measuring region on the X-ray film 22 is set previously for a bone-morphometric data processing unit 32, which will be described afterward, it is possible to shorten the measurement time by rapid-feed portions of the X-ray film other than a portion having the object measuring region, namely, a portion including the second metacarpal bones and the aluminum step wedge, to store only digital data representing the measured densities of the object measuring region.

The transmitted light-quantity data of the image of the sample bone read by the automatic image read unit 31 is converted into digital signals by the A/D converter 49, the digital signals are corrected and processed by the DSP 47, and then the corrected and processed data is sent out as bone-morphometric data representing different positions in the image from the DSP 47. Naturally, the bone-morphometric data may be analog data of the respective images of the sample bone and the aluminum step wedge.

The configuration and operation of the bone-morphometric data processing unit 32 will be described hereinafter.

The bone-morphometric data of the respective images of the sample bone and the aluminum step wedge read by the automatic image read unit 31 is applied to the bone-morphometric data processing unit 32 for storage and processing.

The bone-morphometric data processing unit 32 comprises an image I/O unit 55, an image memory 56 for storing the bone-morphometric data received through the image I/O unit 55, an interface PIO 57 interconnecting the automatic image read unit 31 and the bone-morphometric data processing unit 32, a microprocessor (a MPU or a CPU) 60, a ROM 61, a RAM 62, a bus 58 connecting the ROM 61 and the RAM 62 to the MPU 60, a keyboard interface (KBI/F) 63, a keyboard 26 connected through the keyboard interface 63 to the bus 58, display means comprising of a CRT 23 and a display controller (CRTC) 64, output means comprising a printer 25 and a printer interface (PR I/F) 65, a RS-232C 66 and a MODEM 67. The RS-232C 66 and the MODEM 67 are provided, when necessary, for communication between the bone-morphometric data processing unit 32 and a morphometric bone assay system, which will be described afterward.

It is known from experiments that the roentgenographic image of the sample bone can be formed in a 142 mm×57 mm area and the required capacity of the image memory 56 is 1.9 MB when the sample bone is the second metacarpal bone, and the required capacity of the image memory 56% for storing the data of the aluminum step wedge is 0.1 MB. Accordingly, a sufficient capacity for the image memory 56 is on the order of 2 MB. The MPU 60 may be a commercial 16-bit MPU to address the image memory 56.

The operation of the bone-morphometric data processing unit 32 will be described hereinafter. The bone-morphometric data of the image formed on the X-ray film 22, read by the automatic image read unit 31 and received by the image I/O unit 55 is stored in the image memory 56. The bone-morphometric data stored in the image memory 56 is applied through the bus 58 and the display controller 64 to the CRT 23 to display the picture of the sample bone on the screen 23a of the CRT 23, preferably, in an enlarged size, as shown in FIG. 4.

Figure 4:
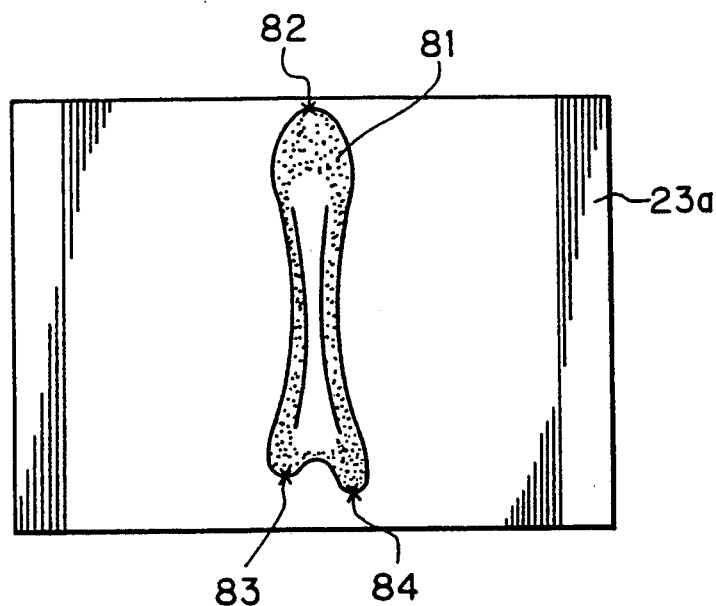
FIG. 4 is a plan view of a picture of a sample bone displayed on a display unit included in the bone-morphometric apparatus of FIG. 1.

Referring to FIG. 4, a picture 81 of the second metacarpal bone is displayed on the screen 23a of the CRT 23. Three reference points 82, 83 and 84 are set at the caput and epiphyses of the second metacarpal bone by moving the cursor in the screen by the picture display means including the CRT 23 (for example, a 7 in., 640-dot, 400-line CRT) and the point input unit 24 (FIG. 1) to specify measuring regions in the picture 81 of the second metacarpal bone.

As stated above, the point input unit 24 is means for applying signals to specify a position on the screen, such as cursor-locating control means, light-pen input means, touch-panel input means, push-button input means or mouse input means. The point input unit 24 is connected to the bus 58.

When carrying out a bone-morphometric operation, a region to be measured is determined in the image 22a of the sample bone stored in the image memory 56 with reference to the reference point specified by the point input unit 24, the bone-morphometric data relating to the region in the image of the sample bone is read out, and then the MPU 60 manipulates the bone-morphometric data according to an operation program stored in the ROM 61 for bone-morphometric operation, which will be described afterward. The RAM 62 stores the data that will be utilized by the MPU 60 during the execution of the operation program.

Figure 5:
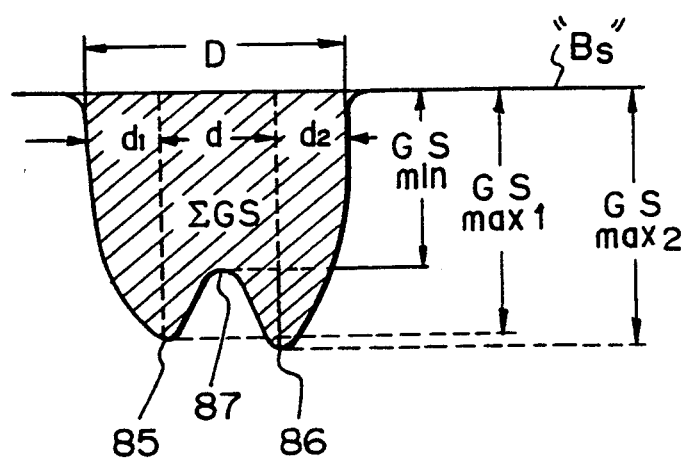
FIG. 5 is a graphical view typically illustrating an arithmetic process in accordance with the present invention for bone morphometry.

FIG. 5 shows a concrete operation process for bone-morphometric operation. Other generally known bone-morphometric techniques employing the MD method, such as those disclosed in Japanese Unexamined (Kokai) Patent Publication Nos. 59-8935, 59-49743, 60-83646, 61-109557 and 62-183748, may be used. When analog image data representing both the respective images of the sample bone and the aluminum step wedge are stored in the image memory 56, the analog image data of the sample bone may be converted into data expressed by the thickness of the aluminum step wedge.

FIG. 5 shows a pattern representing the image data of the image 81 of the second metacarpal bone on a transverse line crossing the middle point of the longitudinal axis of the image 81. In FIG. 5, D is the width of the bone, a hatched area expresses bone density, $d_1$ and $d_2$ are the widths of bone cortices, d is the width of the bone marrow, $GS_{min}$ corresponds to the minimum value of a valley 87 between peaks 85 and 86 and is the index of the density of (the bone cortex)+(the bone marrow), $GS_{max}1$ and $GS_{max}2$ are the respective maximum values of peak portions, and $\Sigma\ GS$ is the total area of the hatched area with respect to the width D. (Kotsu Taisha, Vol. 4, pp. 319–325 (1981)) That is, the operating means 60, 61 and 62 compute the caput 82 and the perpendicular bisector of a line connecting the epiphyses 83 and 84 to detect the intersection point and use the results of computation for the operation of the stored data to determine the values of D, $D_1$, $d_2$, d, $GS_{min}$, $GS_{max}1$, $GS_{max}2$ and $\Sigma$ GS. Then, the operating means 60, 61 and 62 compute, for example, bone cortex width index MC1 ($=(d_1+d_2)/2$), bone marrow width d, an index $GS_{min}$ indicating the quantity of bone mineral of (the bone cortex)+(the bone marrow), an index $GS_{max}$ ($=(GS_{max}1+GS_{max}2)/2$) indicating the quantity of bone mineral of the bone cortex, and an index $\Sigma$ GS/D indicating the mean quantity of bone mineral per bone width by using the data obtained by the operation shown in FIG. 5. The results of the computation may be applied through the printer interface 65 to the printer 25 or may be stored in storage means similar to the RAM 62.

The printer 25 is an example of the output means and may be a dot printer, a thermal printer, a laser printer or a video printer to provide the results of the computation in hard copies. Practically, preferable output means are CRTs, particularly, display means capable of displaying the bone density distribution in colors.

In the foregoing example, the bone-morphometric indices are calculated by using only the stored data representing the image data on the transverse line crossing the middle point of the longitudinal axis of the image. The bone-morphometric indices may be determined by averaging bone-morphometric indices for image data on transverse lines extending parallel to and on the opposite sides of the transverse line crossing the middle point of the longitudinal axis. The operating means 60, 61 and 62 may be such as disclosed in U.S. Pat. No. 4,721,112 which performs the bone morphometry of regions of a long bone and determines the bone density distribution of the long bone on the basis of the measured results.

This bone-morphometric apparatus embodying the present invention is capable of automatically carrying out the bone-morphometric operation using a roentgenogram at a high efficiency, scarcely requiring manual operation. The employment of the automatic image read means including the linear light source for illuminating the X-ray film, and the linear image detector for detecting the quantity of transmitted light, in particular, improves the efficiency of bone-morphometric operation significantly. The adjustable linear light source enables accurate bone morphometry regardless of the variation in the contrast level of the roentgenogram.

Figure 8:
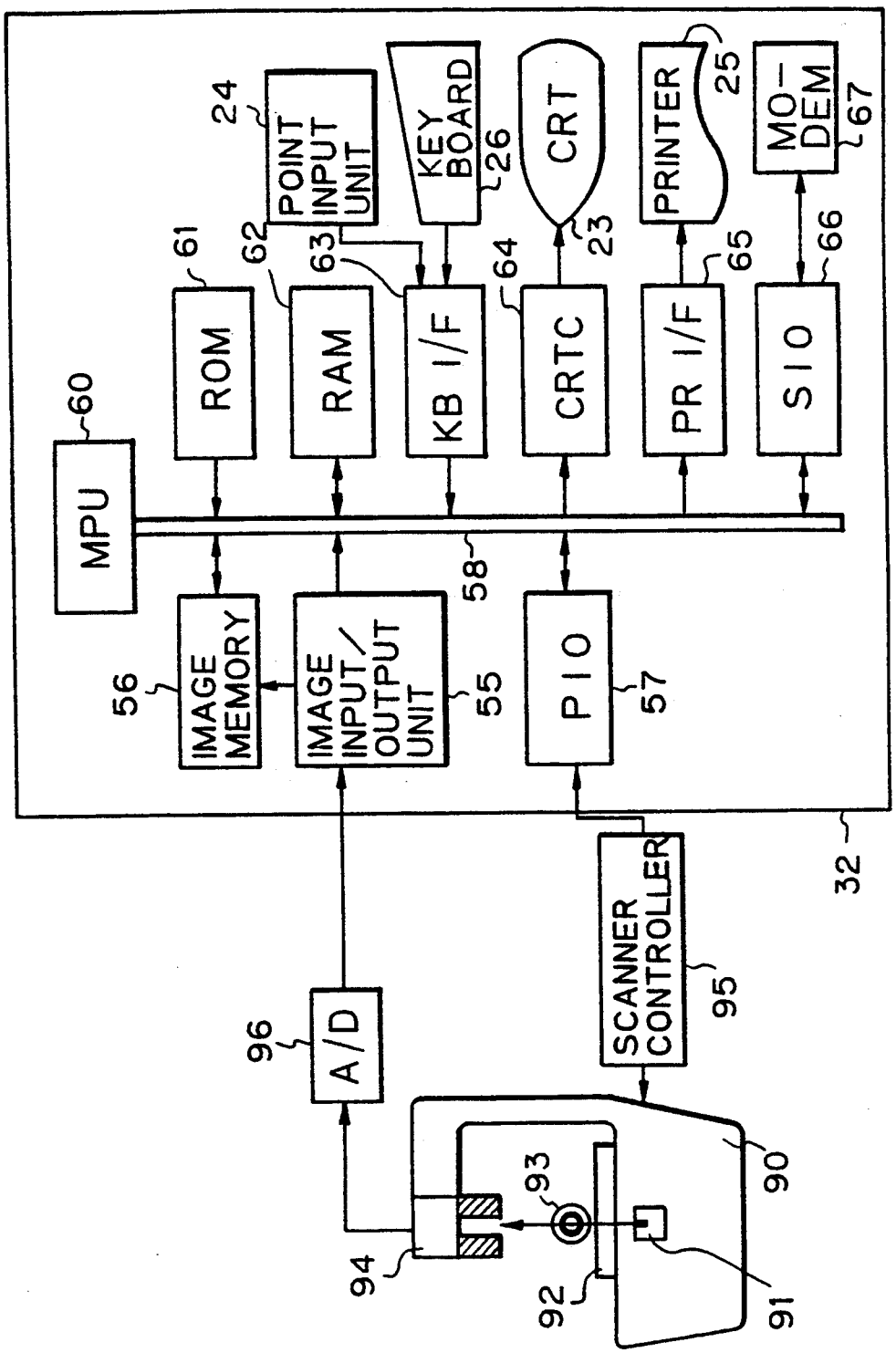
FIG. 8 is a block diagram of a radiographic apparatus for bone morphometry, embodying the present invention.

FIG. 8 is a block diagram of a bone-morphometric apparatus in another embodiment according to the present invention, which uses a radiographic image produced by irradiating a sample bone with radioactive rays instead of a roentgenographic image for bone morphometry.

Referring to FIG. 8, a radiographic image forming apparatus 90 comprises a radiation source 91 which radiates radioactive rays, such as gamma rays, in a predetermined direction, a movable table 92 for supporting a sample 93, for example, the human hand, a radiation detector 94 for detecting the quantity of radioactive rays transmitted through the sample 93, a scanner controller 95 for controlling the movement of the movable table 92 so that the sample 93 may be scanned entirely by the radioactive rays, and an A/D converter 96 which converts, similarly to the afore-mentioned A/D converter 49, analog detection signals provided by the radiation detector 94 into corresponding digital detection signals to be delivered. The A/D converter 96 of the radiographic image forming apparatus 90 sends out digital data representing the radiographic image of the sample 93. A bone-morphometric data processing unit 32 for processing the output digital data of the radiographic image forming apparatus 90 for bone morphometry is the same as that of the foregoing embodiment, and hence the component parts of the bone-morphometric data processing unit 32 corresponding to those of the bone-morphometric data processing unit 32 of the foregoing embodiment shown in FIG. 3 are denoted by the same reference characters.

A further improved bone-morphometric method and a further improved bone-morphometric apparatus will be described hereinafter with reference to those of the foregoing embodiment of the present invention.

First, a method of accurately carrying out bone morphometry by combining the smoothing of the density pattern of the image of a sample bone and the conversion of the density pattern into density data expressed by the thickness of a standard block, and an apparatus for carrying out the method will be described.

The inventors of the present invention found, through intensive studies of ways to perform bone morphometry accurately and rapidly, that smoothing in a direction perpendicular to the direction of a scanning line for bone morphometry and, if necessary, the combination of such smoothing and smoothing in the direction of the scanning line are effective.

In the following description, a roentgenogram is used and reference is made with FIGS. 2, 3, 5 and 9 to 11.

Digital signals corresponding to the quantity of transmitted light transmitted through the roentgenographic image of a sample bone formed on a X-ray film are stored as bone-morphometric data in the image memory 56 of the bone-morphometric data processing unit 32 in relation with positions on the X-ray film.

The bone-morphometric method in this embodiment obtains a first smoothed pattern of the image of the sample bone by obtaining density patterns along substantially parallel scanning lines around an object measuring region and smoothing the density patterns respectively at the corresponding positions. The bone-morphometric apparatus has smoothing means. The density pattern is a representation of quantities of transmitted light or transmitted radiation at points on the measuring line or a digital representation of quantities of transmitted light or transmitted radiation. Smoothing is obtaining the arithmetic mean or the weighted mean of quantities of transmitted light or transmitted radiation.

Figure 9:
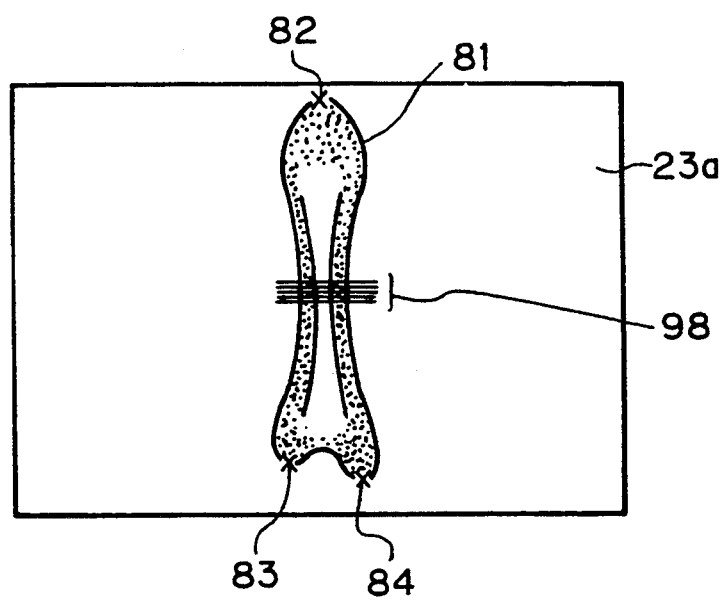
FIG. 9 is a plan view, similar to FIG. 4, of a picture of a sample bone displayed on a display unit.

FIG. 9 shows a picture 81 of a second metacarpal bone displayed on the screen 23a of the CRT 23 (display means) as a concrete example of a first smoothed pattern. Reference points 82 to 84 specified by means of the point input unit 24 are shown on the picture 81.

When the object measuring region is the middle portion of the second metacarpal bone with respect to the reference points 82, 83 and 84 in FIG. 9, the first smoothed pattern is obtained by scanning the picture along a plurality of scanning lines 98 extending at equal intervals of 65 $\mu$m in a very narrow range of 0.1 mm or less about the object measuring region to obtain patterns of quantities of transmitted light on the scanning lines and subjecting the patterns to a smoothing process, such as the calculation of the weighted mean. Such a smoothing process eliminates random noise in the pattern of the quantity of transmitted light effectively without reducing the spatial resolution.

The number of the scanning lines 98 for smoothing may be determined in view of the following conditions. A quantity of transmitted light measured by an automatic image read means having a resolution on the order of 65 μm includes random noise on the order of ¼ to 1/5 of the thickness step (1 mm) of an aluminum wedge, i.e., 0.2 to 0.25 mm. Although the greater number of the scanning lines 98 is desirable, it is simple and preferable to average the data of quantities of transmitted light on about twenty-one scanning lines in the same weighting, because an excessively large number of scanning lines 98 makes the object measuring region ambiguous and the noise must be reduced to a value below 0.05 mm.

A first smoothed pattern of the quantity of transmitted light for the sample bone thus obtained is converted on the basis of the thickness of the standard block and the quantity of transmitted light to obtain a converted pattern represented by the thickness of the standard block. The effect of the difference in roentgenographic conditions on the bone-morphometric data can effectively be eliminated by converting the pattern of the quantity of transmitted light into a pattern represented by the thickness of the standard block prior to arithmetic processing.

The apparatus of FIG. 8 uses an image formed by detecting transmitted radiation. In such a case, it is practically desirable to store the relation between the thickness of a standard sample, i.e., a phantom, and the quantity of transmitted radiation in advance and to obtain a converted pattern on the basis of the relation.

According to the present invention, if necessary, a second smoothed pattern may be produced by subjecting such a converted pattern or the first smoothed pattern of the transmitted light to a smoothing process, such as the calculation of the moving average of data at a plurality of points on the scanning lines. The combination of the first and second smoothing processes enables the efficient elimination of high-frequency noise in a plane and accurate operation for bone morphometry. In practical bone-morphometric operation, it is preferable to employ a digital filter capable of filtering spatial frequencies exceeding a frequency corresponding to a period of 0.5 mm, because variations of periods not greater than 0.5 mm are unnecessary. When the second smoothed pattern is obtained from the first smoothed pattern, the second smoothed pattern must be converted into a converted pattern. Practically, it is preferable to obtain converted patterns respectively corresponding to the first and second smoothed patterns.

The bone-morphometric apparatus in accordance with the present invention comprises first smoothing means, converting means and, if need be, second smoothing means. Concretely, those means comprises the MPU 60, the ROM 61 and the RAM 62 of the aforesaid bone-morphometric data processing unit 32.

Figure 12A:
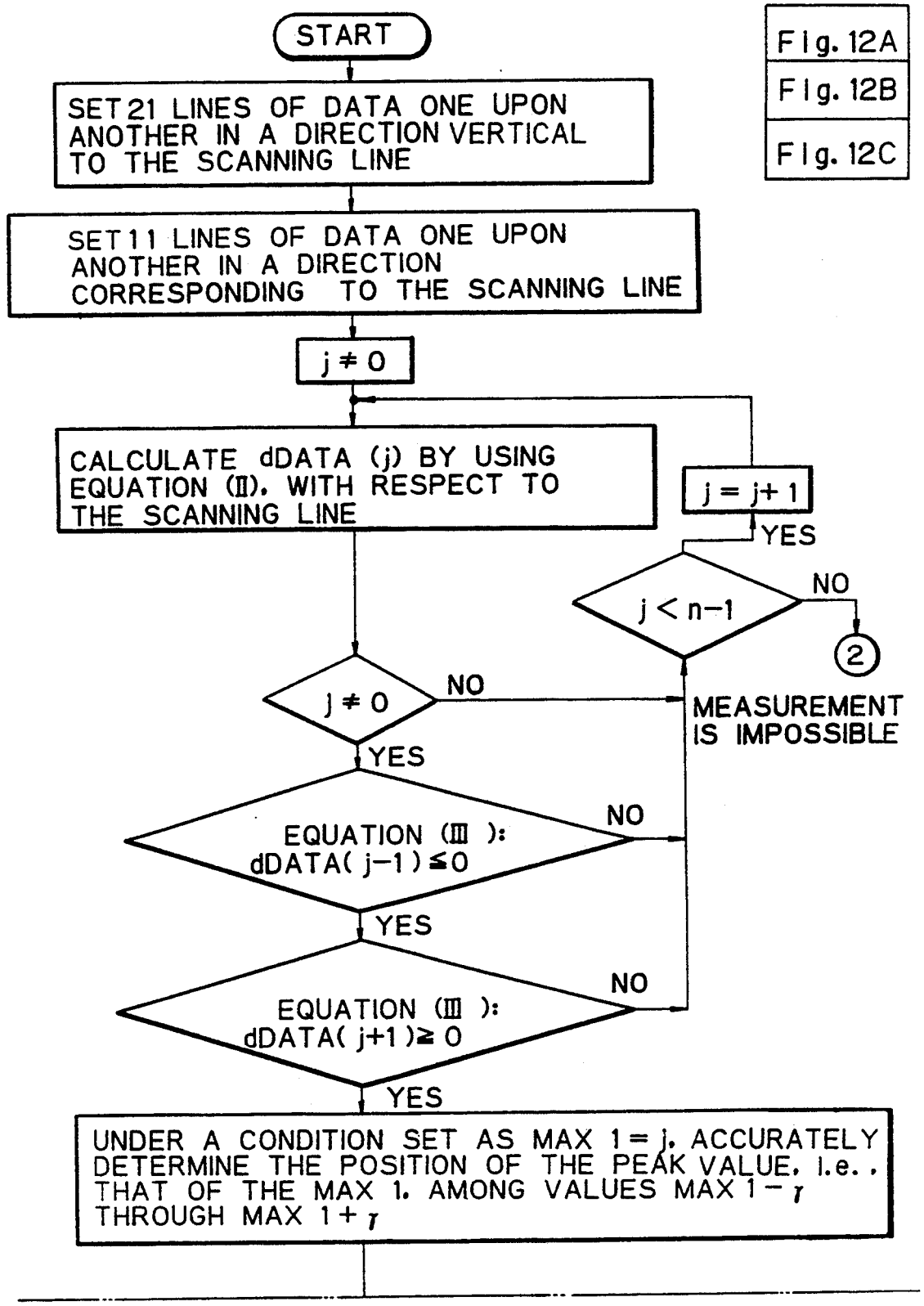
FIGS. 12A, 12B and 12C are flow charts of a pattern smoothing process, a peak detecting process and a baseline detecting process in accordance with the present invention, respectively.
Figure 12B:
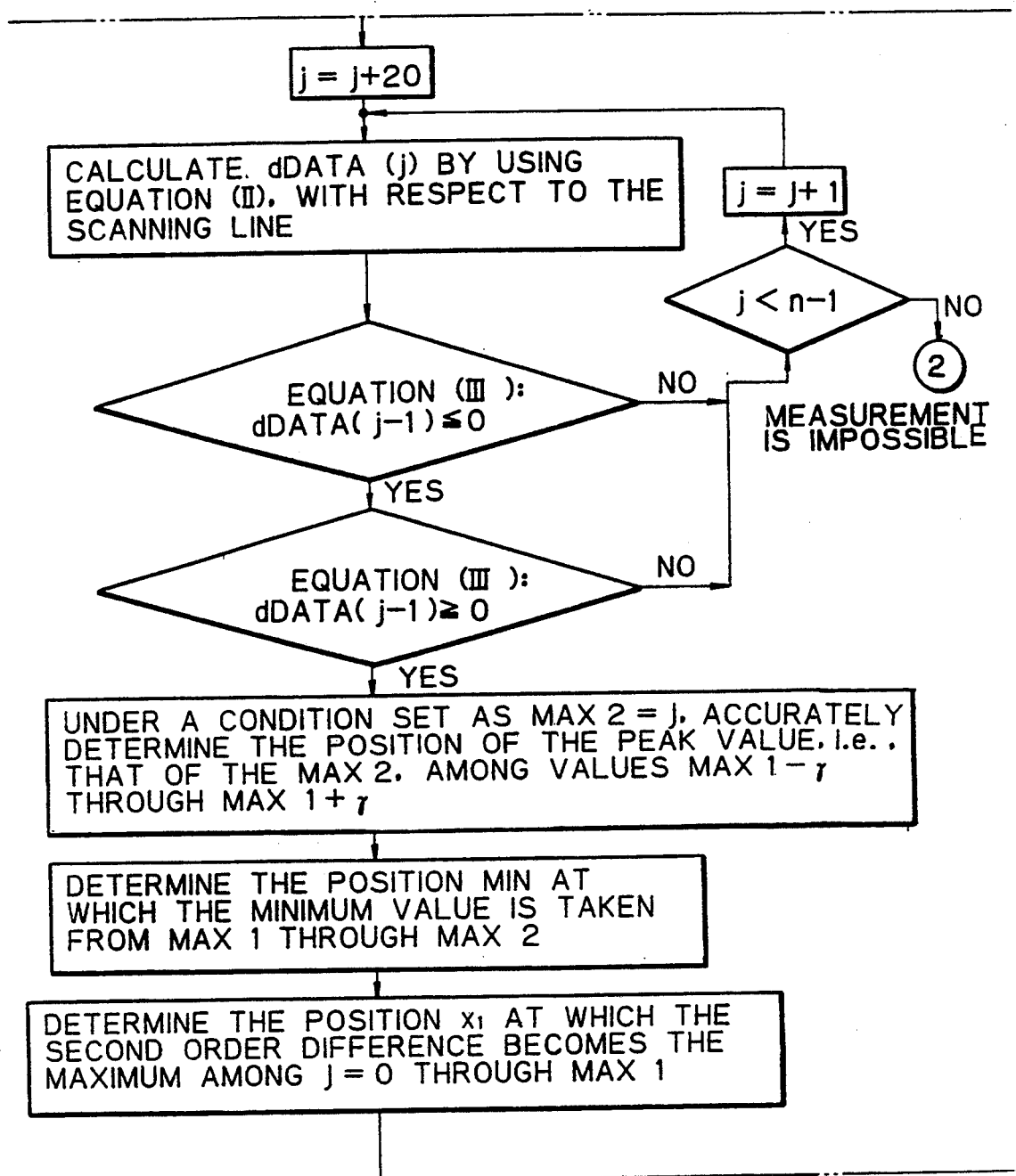
Figure 12C:
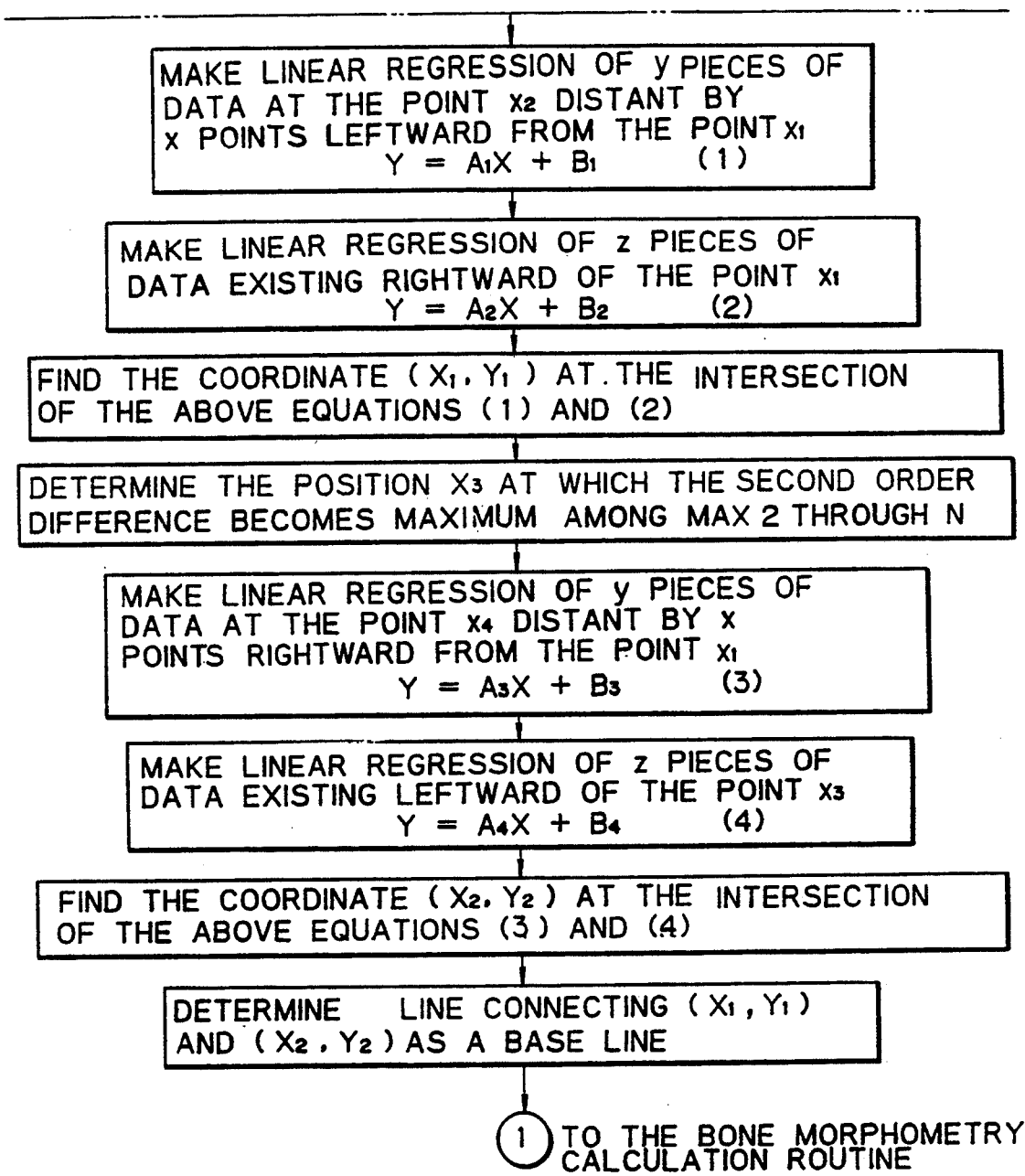

The aforesaid bone-morphometric operation (FIG. 5) is performed on the basis of the thus obtained smoothed pattern or the converted pattern. Shown in FIGS. 12 (FIGS. 12A–12C) is a flow chart of the foregoing smoothing process to be performed by the MPU 60, the ROM 61 and the RAM 62 of the bone-morphometric data processing unit 32. In carrying out the smoothing process, the MPU 60 executes operation according to a predetermined program stored in the ROM 61, and the RAM 62 stores the data that will be utilized by the MPU 60 during the execution of the program.

The bone-morphometric apparatus in this embodiment detects peaks, such as peaks 85 and 86 shown in FIG. 5, automatically through the following procedure. The gradients of tangents to the profile of the image in a global region is examined so that small peaks attributable to noise or the like may not erroneously be detected as peaks, and then a peak point is set at a position where the gradient is zero, namely, where the sign of the gradient changes from positive to negative or from negative to positive.

A peak point on an image formed on an X-ray film is detected by the following method.

First, when detecting the first peak 85, a smoothness differential is calculated by using $$d\text{DATA}(j) = \sum_{i=j-\alpha-\beta}^{j-\alpha} \text{DATA}(i) - \sum_{i=j+\alpha}^{j+\alpha+\beta} \text{DATA}(i) \quad \text{(II)}$$

A position where DATA(j) meeting the following conditions is maximum is in the vicinity of the peak.

$$d\text{DATA}(j-1) \leq 0 \text{ and } d\text{DATA}(j+1) \geq 0 \quad \text{(III)}$$

In Expressions (II) and (III), DATA(j) is the quantity of transmitted light transmitted through a portion of the image corresponding to a position j, and $\alpha$ and $\beta$ are constants determined preferably with reference to the resolution of the apparatus, the magnitude of the noise component or the size of the region. Practically, with an apparatus having a spatial resolution on the order of 65 μm, $\alpha=4$ and $\beta=17$. The peak 85 can be further accurately detected by detecting the maximum value in the data of a region around the peak 85 again. Once the peak is detected, it is preferable to recognize the detected peak as a peak if any peak is not detected in a region $\gamma$ after the former peak has been detected in order that the peak 86 is not recognized as the first peak. The size of the region $\gamma$ is dependent on the distance between the adjacent peaks. Practically, the value of the region $\gamma$ is on the order of 20. The peak 86 is detected likewise. The peak 87 corresponds to the minimum in a region between the peaks 85 and 86.

Figure 10:
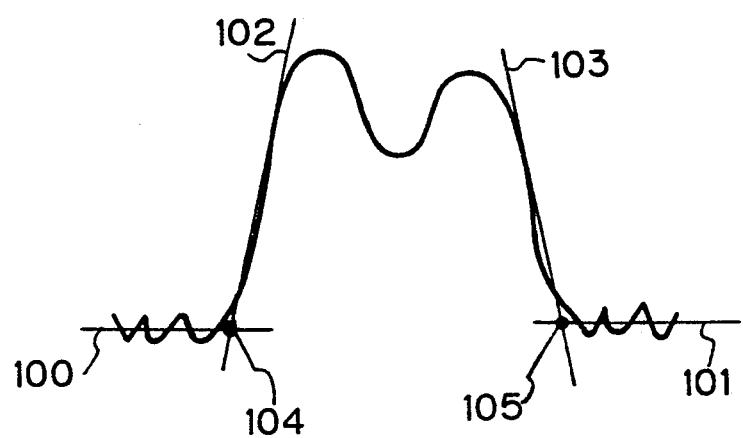
FIG. 10 is a graph corresponding to the inversion of the pattern shown in FIG. 5.
Figure 11:
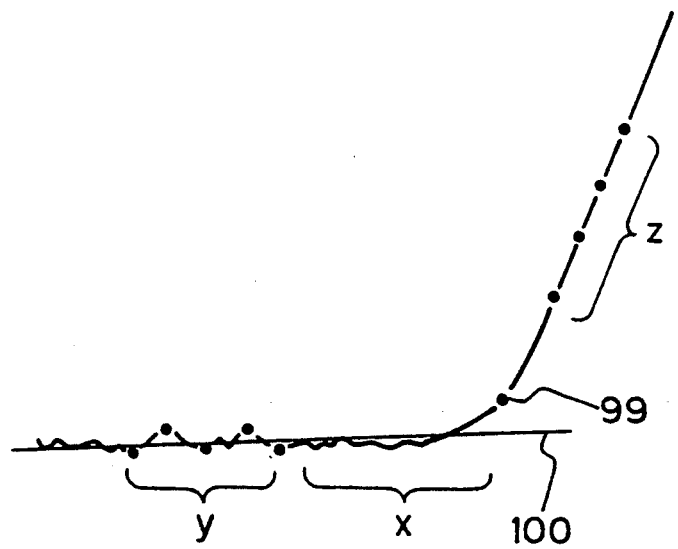
FIG. 11 is a graph showing the left end portion of the pattern shown in FIG. 10 in an enlarged view.

A bone-morphometric method or apparatus in a preferred embodiment according to the present invention determines the base line Bs (FIG. 5) by the following procedure. Referring to FIGS. 10 and 11, an inflection point 99 is determined on the basis of a fact that the second order difference is maximum in one of the rising portions of the curve, and then a line 100 for the left soft part is determined by linear regression analysis using y pieces of data after x pieces data outward from the inflection point 99. A line 101 for the right soft part is determined likewise. Then, contact lines 102 and 103 each having a maximum gradient are determined by linear regression analysis using z pieces of data inward from the inflection point 99 for each line. The intersection point 104 of the lines 100 and 102 and the intersection point 105 of the lines 101 and 103 are connected to determine the base line Bs (FIG. 5).

Practically, x=8, y=10 and z=16 are desirable.

The bone-morphometric method and the bone-morphometric apparatus embodying the present invention eliminates effectively the effect of differences in the conditions of radiographic photographing operation and noise attributable to the X-ray film to enable accurate bone morphometry.

A bone-morphometric apparatus employing picture display means, such as the CRT 23 (FIG. 3) for displaying the picture of the image of a sample bone, provided with mark display means capable of displaying and erasing marks, such as a reference point for indicating a reference position, and lines, in the monochromatic picture will be described hereinafter. The indication and erasing of marks will be described hereinafter with reference to FIGS. 3, 4 and 13 on an assumption that the bone-morphometric apparatus and the bone-morphometric method embodying the present invention are applied to the bone morphometry of the roentgenograms of a sample bone and a standard block.

In this embodiment, the bone-morphometric apparatus is provided with mark display means capable of reversing the density of a monochromatic picture. Preferably, a picture display means capable of displaying binary pictures, such as characters and diagrams, as well as a toned picture. The CRT 23 meets such a requirement.

Figure 13:
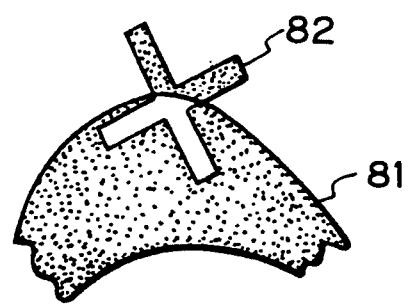
FIG. 13 is a plan view showing an enlarged mark formed by reversing a mark 82 shown in FIG. 4 as displayed on a screen, in an embodiment employing means for both writing and erasing marks including a reference point and a reference line.

In FIG. 13, a reference point formed by reversing the reference point 82 shown in FIG. 4 is displayed on the screen 23a.

The image storage means (image memory 56) of the bone-morphometric apparatus in this embodiment stores image data for displaying a picture of 400 (vertical) ×600 (horizontal) picture elements. The density of each picture element is expressed by 8-bit gradation. The capacity of the image storage means is dependent on the accuracy of the screen, and the number of picture elements and the expression of the density of each picture element need not be limited to the foregoing values.

A specific position on the monochromatic picture is marked with a point by the following procedure.

Picture elements showing the position to be marked are specified, and then the densities of the picture elements are obtained. The densities of the picture elements are subjected, in combination with 255, to an exclusive OR operation for density reversal. Then picture elements respectively having reversed densities are displayed instead of the original picture elements, respectively, to indicate the point. When the density of the original picture element is, for example, 196, the density of the corresponding reversed picture element is 59.

Likewise, the mark can be erased by reversing the reversed picture elements again by the same reversing procedure.

The picture element can be reversed by deriving the one's complement of the density value, however, in view of processing rapidness, the procedure of the present invention is more advantageous.

Marks which can be formed by dots, such as lines, circles and symbols, may be used as well as points.

As is obvious from the foregoing description, the bone-morphometric apparatus in this embodiment is capable of readily indicating marks on the monochromatic picture and readily erasing the marks to restore the original monochromatic picture. Particularly, the employment of the density reversing means simplifies the hardware of the apparatus and enables the use of a memory having a comparatively small capacity.

A liquid crystal display (LCD) or a plasma display may be used instead of the CRT employed as picture display means by this embodiment, however, to obtain a high resolution picture display, the CRT is most appropriate.

A bone-morphometric method and a bone-morphometric apparatus in a preferred embodiment capable of adjusting the quantity of light emitted by the light source according to the condition of a roentgenogram will be described hereinafter with reference to FIGS. 2, 3, 5, 14A and 14B.

The bone-morphometric apparatus in this embodiment illuminates an X-ray film carrying the images of a sample bone and an aluminum step wedge, and measures the quantity of transmitted light transmitted through the images for bone morphometry. The basic features of this bone-morphometric apparatus are to determine a region in the image of the aluminum step wedge that transmits a quantity of light meeting a predetermined condition, to make a first decision on whether the range of quantity of transmitted light transmitted through an object measuring region in the image of the sample bone is included in the range of quantity of transmitted light transmitted through the aluminum step wedge, to make a second decision on whether the quantity of transmitted light transmitted through the object measuring region and the corresponding quantity of transmitted light transmitted through the aluminum step wedge are detected in a predetermined resolution, and to adjust the quantity of illuminating light for illuminating the X-ray film on the basis of the results of the second decision.

When the quantity of illuminating light must be increased for light-quantity adjustment, the quantity I of transmitted light transmitted through the aluminum step wedge greater than and approximately equal to the maximum quantity of transmitted light transmitted through the object measuring region is determined, and the quantity of illuminating light is adjusted so that the quantity I of transmitted light is not greater than and nearly equal to a predetermined value $I_{max}$.

When the quantity of illuminating light needs to be reduced, a portion of the object measuring region through which a quantity of light exceeding the predetermined value $I_{max}$ is transmitted is detected, an appropriate quantity of illuminating light is estimated on the basis of the size of the portion of the object measuring region and the quantity of illuminating light is adjusted to the appropriate quantity.

The above-mentioned decisions and the adjustment of the quantity of illuminating light are achieved by the following method. The X-ray film is illuminated by a quantity of illuminating light determined previously according to the examinee's sex and age and the quantity of transmitted light transmitted through the image of the aluminum step wedge is measured with the X-ray film positioned at a predetermined position.

Effective regions in the images of the steps of the aluminum step wedge, namely, regions which can effectively be discriminated from each other, are determined on the basis of the relation between the measured quantity of transmitted light and the respective thicknesses of the steps of the aluminum step wedge. In view of bit errors in A/D conversion, the difference in the quantity of transmitted light as expressed by digital signals provided by the A/D converter 49 between the adjacent regions in the image of the aluminum step wedge corresponding to the adjacent steps of the aluminum step wedge must be not less than two digits and the quantity of transmitted light must not saturate the image, when the measured quantity of transmitted light is converted into digital signals by the A/D converter 49. The maximum quantity $I_1$ of transmitted light transmitted through the image of the aluminum step wedge and the minimum quantity $I_2$ of transmitted through the aluminum step wedge are determined. The maximum quantity $S_1$ of transmitted light and the minimum quantity $S_2$ of transmitted light among those of transmitted through the image of the object measuring region of the sample bone are determined.

A query is made for the first decision to see if $S_1 \leq I_1$. When the quantity of illuminating light is excessively large, the response to the query is negative, and thus the quantity of illuminating light must be reduced. When the response is affirmative, a query is made to see if $S_2 \geq I_2$. When the quantity of illuminating light is excessively small, the response to the query is negative, and thus the quantity of illuminating light must be increased. When $S_1 > I_1$ and $S_2 < I_2$, bone morphometry is impossible regardless of the quantity of illuminating light. When bone morphometry is impossible, information is displayed on the display to that effect and the X-ray film is ejected.

When both the conditions $S_1 \leq I_1$ and $S_2 \geq I_2$ are satisfied, the second decision is made. That is, a quantity $I_1'$ of transmitted light transmitted through the aluminum step wedge greater than and nearest to the quantity $S_1$ of transmitted light, and a quantity $I_2'$ of transmitted light transmitted through the aluminum step wedge smaller than and nearest to the quantity $S_2$ of transmitted light are selected. Then, digital values corresponding to the respective thickness of the steps of the aluminum step wedge corresponding to the range of $I_1'$ to $I_2'$ are determined and the minimum value $\Delta I$ among the digital values is selected. For example, when the difference in thickness between the adjacent steps of the aluminum step wedge is 1 mm and the required resolution is 0.2 mm or less, $\Delta I$ must be five digits or greater, preferably, seven digits or greater. When $\Delta I$ must be, for example, seven digits or greater, a query is made to see if $\Delta I \geq 7$. When the response is affirmative, it is considered that the X-ray film 22 is illuminated by an appropriate quantity of illuminating light, and the subsequent steps of bone morphometry are performed. If the response is negative, the quantity of illuminating light must be increased.

The adjustment of the quantity of illuminating light will be described hereinafter. When it is decided that the quantity of illuminating light is insufficient, the quantity of illuminating light is adjusted so that the quantity $I_1'$ of transmitted light is not greater than and nearest to the predetermined value $I_{max}$, and then the measurement is performed again. Preferably, a value corresponding to the predetermined value $I_{max}$ is in the range of 95 to 98% of the saturation level of the image detector 42 or the A/D converter 49.

When the quantity of illuminating light is excessively large, the length of a measured portion where the quantity of transmitted light is greater than the predetermined value $I_{max}$ is measured, namely, the number of dots on the CCD detector or the like corresponding to the length of the portion is counted. The relationship between the count of dots and (quantity of illuminating light) - (appropriate quantity of illuminating light) for the second metacarpal bone is shown in Table 1.

TABLE 1

| | Dot Count | | | | | | | |
|---|---|---|---|---|---|---|---|---|
| | 5 | 12 | 20 | 50 | 80 | 100 | 130 | 150 |
| Quantity of Illuminating Light | 2 | 3 | 4 | 5 | 6 | 7 | 8 | 9 |
| Quantity of Transmitted Light | | | | | | | | |

The appropriate quantity of illuminating light is estimated from the dot count on the basis of the relationship shown in Table 1. When the dot count of a portion where the quantity of transmitted light exceeds the predetermined value $I_{max}$ is zero, the quantity $I_{11}$ of transmitted light corresponding to a step of the aluminum step wedge thicker by one common thickness difference than the step corresponding to the quantity $I_1$ of transmitted light is estimated by using a formula $$I_{11} = I_1 - 2.5(I_{12} + I_{13})$$

where $I_{12}$ is the quantity of transmitted light corresponding to a step of aluminum step wedge thinner by one common thickness difference than the step corresponding to the quantity $I_1$ of transmitted light, and $I_{13}$ is the quantity of transmitted light corresponding to a step of aluminum step wedge thinner by two common thickness differences than the step corresponding to the quantity $I_1$ of transmitted light. The quantity of illuminating light is adjusted so that the quantity $I_{11}$ of transmitted light is smaller than and approximately equal to, preferably, nearest to the predetermined value $I_{max}$.

If the condition is not improved by the adjustment of the quantity of illuminating light, it is decided that the bone morphometry of the images is impossible, to avoid wasting time for useless measurement. In such a case, it is preferable to display information to that effect and to automatically eject the X-ray film.

When necessary, gamma value $\gamma$ defined by $\gamma = $ (OD (absorbance) variation)/(relative exposure variation) may be used for a third decision. Accurate measurement is possible only when the minimum gamma value $\gamma$ among those for the steps of the aluminum step wedge in the range of $I_1'$ to $I_2'$ is greater than a predetermined gamma value $\gamma_0$. Therefore, it is preferable to use a gamma value in combination with the resolution decision. Preferable gamma value $\gamma$ is in the range of 1 to 4, and preferable predetermined gamma value $\gamma_0$ is in the range of 1 to 2.

A variation of the illuminating time is one method of adjusting the quantity of illuminating light. When the linear light source 41 comprising LEDs is employed as light emitting means, and the linear image detector 42 is employed as transmitted light detecting means, illuminating time can be adjusted by controlling the lighting frequency of the LEDs by a pulse signal generated by a pulse generator. Practically, it is desirable to adjust the quantity of illuminating light by varying illuminating time without changing the intensity of illuminating light for the effective correction to eliminate the influence of the secular change in the characteristics of the linear light source 41 and the linear image detector 42, such as ununiformity of the LEDs in luminance and/or the ununiformity of the CCDs in sensitivity, when the automatic image read means employs the LEDs and CCDs for reading the image.

To improve the measuring efficiency, it is practically advantageous to change a set value representing an illuminating time on the basis of the relation between set value and illuminating time as shown in Table 2 stored in storage means.

TABLE 2

| Set value | 1 | 2 | 3 | 4 | 5 | 6 | 7 |
|---|---|---|---|---|---|---|---|
| Illuminating time | 128 | 256 | 384 | 512 | 640 | 768 | 896 |
| Set value | 8 | 9 | 10 | 11 | 12 | 13 | 14 |
| Illuminating time | 1024 | 1152 | 1280 | 1536 | 1792 | 2048 | 2304 |
| Set value | 15 | 16 | 17 | 18 | 19 | 20 | 21 |
| Illuminating time | 2560 | 3072 | 3584 | 4544 | 5568 | 6592 | 7615 |
| Set value | 22 | 23 | 24 | 25 | 26 | | |
| Illuminating time | 9088 | 11136 | 13632 | 15680 | 18176 | | |

The adjustment of the quantity of illuminating light in accordance with the present invention can be achieved by a bone-morphometric apparatus comprising the automatic image read unit 31 and the bone-morphometric data processing shown in FIG. 3. The MPU 60, ROM 61 and RAM 62 of the bone-morphometric data processing unit 32, and the light source control circuit 45 of the automatic image read unit 31 carries out the functions of the region detecting means, the first decision means, the second decision means and the illuminating light quantity adjusting means. The MPU 60 has the function of the region detecting means and serves also as means for storing given conditions such that the A/D converted value representing the quantity of light corresponding to one common thickness difference of the aluminum step wedge is two digits or greater. The MPU 60 further has the function of the first decision means and serves as storage means for storing $I_1$, $I_2$, $S_1$ and $S_2$ and as comparing means for comparing quantities. The MPU 60 serves also as the second decision means for entering and storing a criterion on which the decision of $\Delta I$ is based. As regards the illuminating light quantity adjusting means, which is one of the features of the bone-morphometric apparatus in this embodiment, the MPU 60 decides a set value for an adjusted quantity of illuminating light, and the light source control circuit 45 sets the luminous intensity of the light source 41. The MPU 60 must have functions for entering and storing $I_{max}$, calculating $I_{11}$, and comparing quantities. The ROM 61 storing the contents of Tables 1 and 2 facilitates the efficient automatic adjustment.

The bone-morphometric apparatus stores the position of the reference point on the picture display means (CRT 23, CRTC 64) entered by the point input means in the storage means, i.e., the RAM 62 before the adjustment of the quantity of illuminating light, reads again the same region in the image formed on the X-ray film by using the adjusted quantity of illuminating light determined on the basis of the result of decision, and then specifies a point in the picture displayed on the CRT 23 with reference to the reference point previously stored in the RAM 62. A series of these operations are carried out by the automatic image read unit 31 controlled by the MPU 60 (FIG. 3). After a new quantity of illuminating light has been set, the X-ray film is fed automatically to locate the respective images of the aluminum step wedge and the object portion of the sample bone at the read position and, when the object portion needs to be indicated by a point, the point previously stored and stored is displayed automatically, which reduces load on the operator.

Figures 2, 14A:
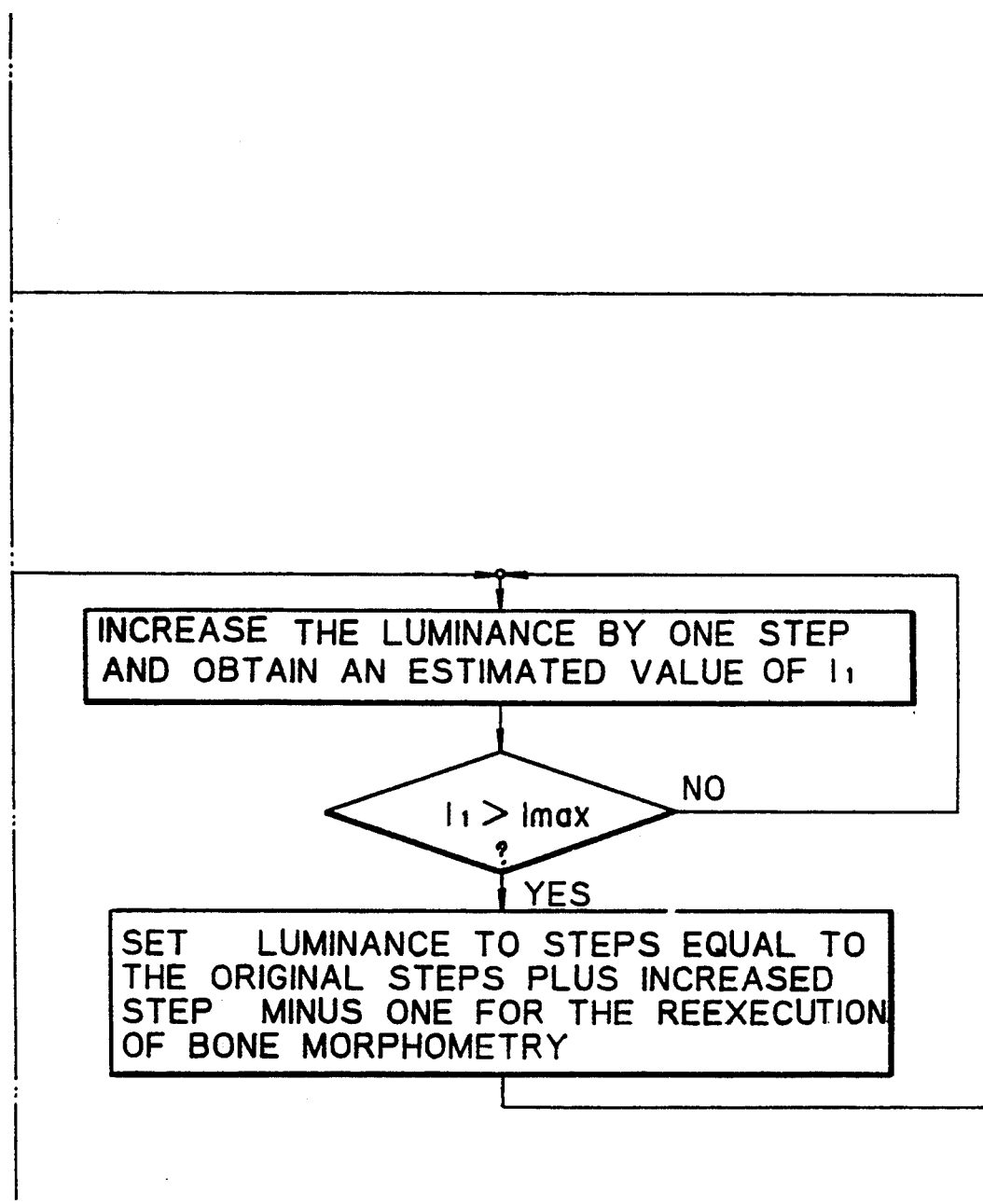
Figure 14B:
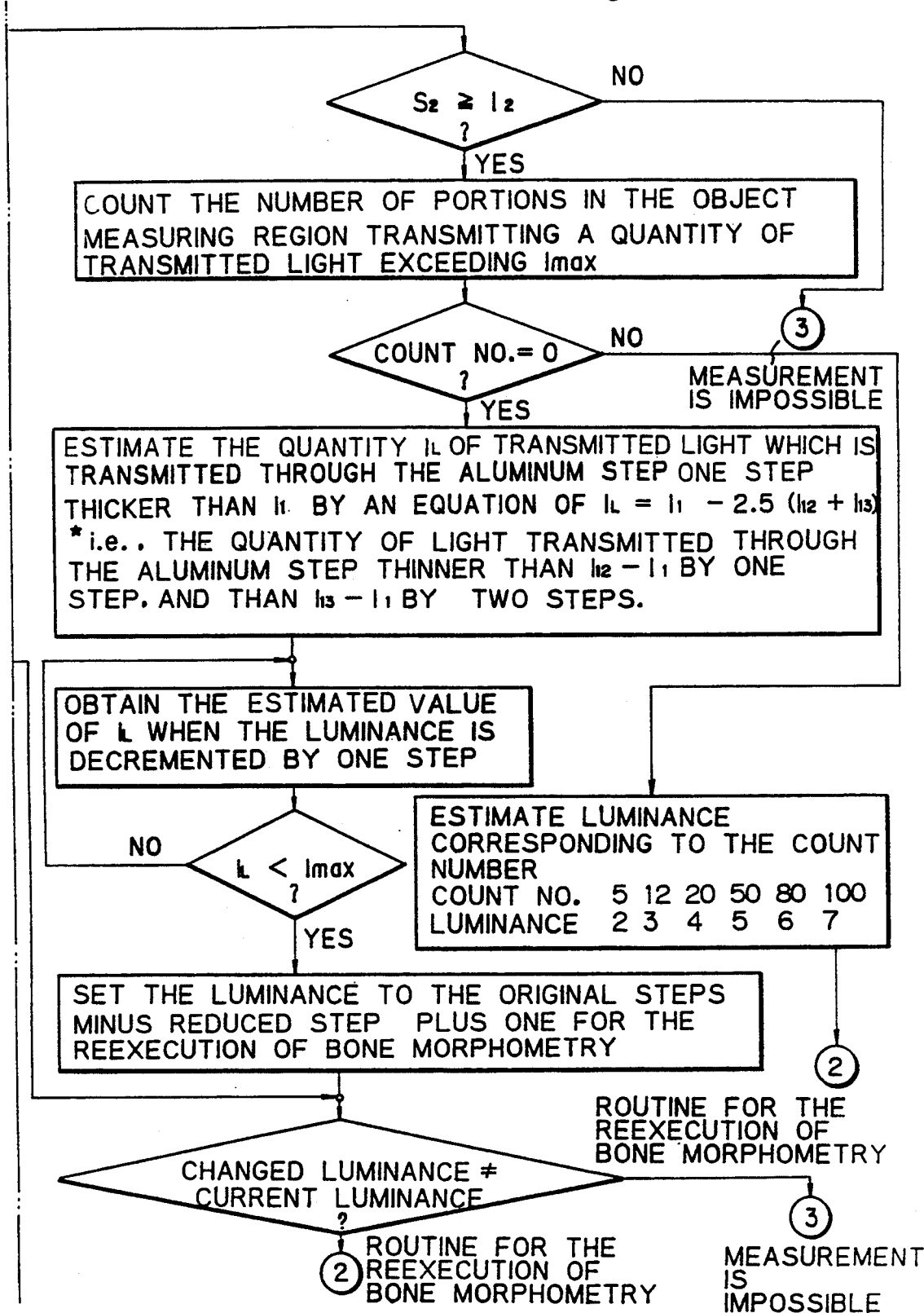

FIGS. 14A and 14B show flow charts of procedures for carrying out the correction of the quantity of illuminating light by the MPU 60, the ROM 61, the RAM 62 and the light source control circuit 45.

A bone-morphometric arithmetic routine ① shown in FIGS. 14A and 14B is executed by the bone-morphometric data processing unit including the MPU 60, the ROM 61 (arithmetic program storage) and the RAM 62 which stores the data that will be utilized by the MPU 60 during the execution of the arithmetic routine.

The results of the bone morphometry are provided by the SIO 66 and the printer 25, i.e., the output means (FIG. 3).

The bone-morphometric method in this embodiment corrects the quantity of illuminating light by a practically simple operation to enable the bone morphometry of images of tones varying in a wide tone range formed on X-ray films, which has been difficult to carry out by the conventional method. The bone-morphometric apparatus in this embodiment employs the illuminating light quantity correcting means to enable the bone morphometry of images of tones varying in a wide tone range formed on X-ray films through a simple operation.

A bone-morphometric apparatus embodying the present invention including an automatic image read unit 31 capable of reading a roentgenographic image formed on an X-ray film at an improved efficiency will be described hereinafter.

The bone-morphometric apparatus in this embodiment is featured by an automatic image read unit for automatically reading roentgenographic images formed on an X-ray film, which comprises: a film loading unit, film feed means, linear image detecting means extended in a direction perpendicular to the film feed direction, image read region setting means for setting a skipping feed distance a along the film feed direction, an effective feed distance b through which the X-ray film is fed for image reading, a distance c from a reference position to an image read region with respect to the direction perpendicular to the film feed direction and an image scanning distance d, and image storage means for storing image data read by the linear image detecting means in the image read region set by the image read region setting means.

The film feed means, linear image detecting means, light source means which emits light for illuminating the film and image read region setting means of the bone-morphometric apparatus in this embodiment may be those respectively corresponding to the means shown in FIG. 3.

Figure 15:
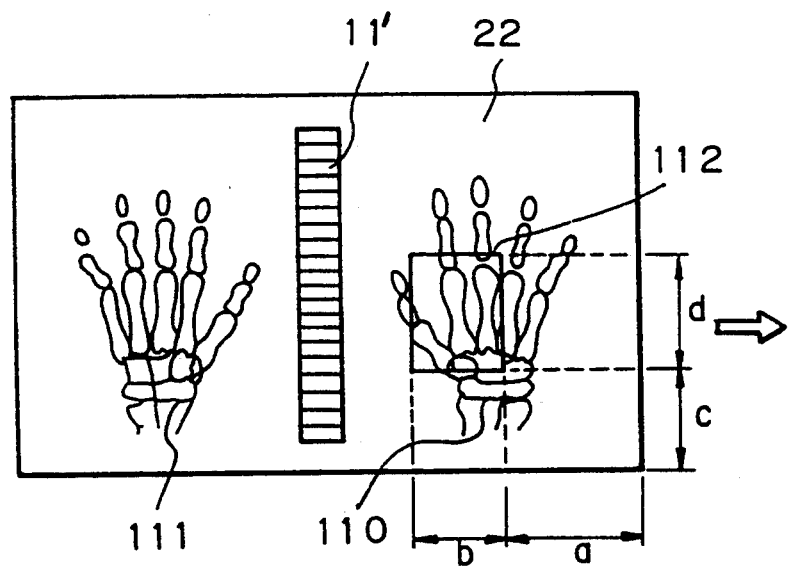
FIG. 15 is a plan view of assistance in explaining a process of setting an object measuring region when reading the roentgenographic images of a sample bone and an aluminum standard step wedge.

Referring to FIG. 15 showing an illustration of assistance in explaining an example of an image read region setting operation for setting an object measuring region in an X-ray film 22, the X-ray film carrying the respective images 11′, 110 and 111 of an aluminum step wedge, i.e., a standard block, the bones of the right hand of the examinee and the bones of the left hand of the same is fed to the right. The second metacarpal bone of the right hand, i.e., the object measuring region, is located in the central portion of an image read region 112 defined by distances a, b, c and d.

With a 253 mm wide and 302 mm long X-ray film, for example, a=46 mm, b=65 mm (1024 lines), c=1 mm (16 picture elements) and d=130 mm (2048 picture elements).

Figure 16:
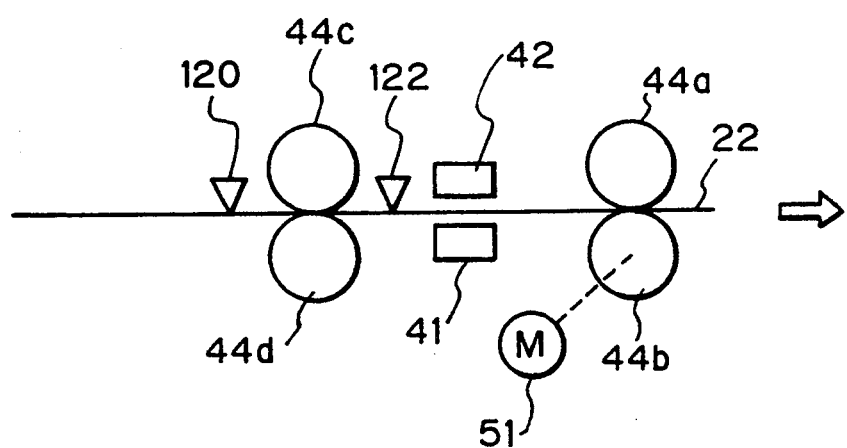
FIG. 16 is a schematic view of X-ray film conveying means, an image illuminating light source and a transmitted light-quantity detecting unit.

Referring to FIG. 16 showing the automatic image read unit 31 shown in FIG. 3 in a further simplified view, while being fed in the direction of the arrow by a pair of feed rollers 44c and 44d and a pair of feed rollers 44a and 44b, the X-ray film 22 is illuminated by the light emitted by a linear light source 41. The quantity of transmitted light transmitted through the X-ray film 22 is detected by a linear image detector 42. In this embodiment, the bone-morphometric apparatus is provided with proper film edge detectors 120 and 122 for detecting the edge of the X-ray film 22.

In this embodiment, the skipping feed distance a through which the X-ray film 22 is fed without being scanned may be a distance a1 from the leading edge of the X-ray film 22 to the front boundary of an object measuring region (FIG. 15) or may be the sum of the distance $a_1$ and a distance $a_2$ equal to the effective distance between the film edge detector 122 and the linear image detector 42 (FIG. 16). When the skipping feed distance a is the sum of the distances $a_1$ and $a_2$, the film edge detector 122 is able to ascertain readily if the X-ray film is fed normally, which is practically advantageous. The leading edge of the X-ray film 22 may be detected by the film edge sensor 120 and the linear image detector 42 as shown in FIG. 16 through the detection of change in the output of the linear image detector 42 comprising CCDs. A quick-feed pulse signal is applied to a stepping motor 51 for driving the feed rollers to feed the X-ray film 22 at a high feed speed, the pulses applied to the driving motor 51 are counted by a pulse counter, and the quick-feed pulse signal is stopped upon the coincidence of the pulse count with a number corresponding to the skipping feed distance a.

Subsequently, a slow-feed pulse signal is applied to the stepping motor 51 to feed the X-ray film 22 intermittently by a distance corresponding to the pitch of scanning lines at a time for image reading. The image data of only the picture elements within a given range along the extension of the linear image detector 42 is stored in an image memory 56. A picture element counter counts the number of picture elements detected by the linear image detector 42.

Upon the coincidence of the picture element count of the picture element counter with a given total count, the image read operation is stopped, the stepping motor 51 is set in a reverse mode, and a quick-feed pulse signal is applied to the stepping motor 51 to eject the X-ray film from the bone-morphometric apparatus. Upon the detection of the leading edge, i.e., the trailing edge when the X-ray film 22 is reversed, by the film edge detector 120, the stepping motor 51 is stopped.

It is preferable, for the accurate setting of the object measuring region on the X-ray film, to use one of the side edges of the X-ray film 22 parallel to the film feed direction as a reference position for setting the distance c, but in practice the use of one side line of a region secured for the film to be fed as the reference position is advantageous, because such a reference position facilitates setting the distance c.

The bone-morphometric apparatus in this embodiment is provided with input means for entering values of the distances a, b, c and d for defining the object measuring region, and storage means for storing the input values of the distances a to d.

It is practically advantageous to use previously determined standard values for the distances a to d entered by input means (keyboard 26) and stored previously in the storage means for the normal bone-morphometric measuring operation and to enter special values greatly differing from the standard values only for a special bone-morphometric measuring operation.

In a modification, the automatic image read unit of the bone-morphometric apparatus may be provided with object measuring region setting means for setting the distances a, b, c and d for defining each of an object measuring region and a calibration image region in an X-ray film, and image storage means for storing images read respectively from the object measuring region and the calibration image region.

Thus, the automatic image read unit is capable of entering values for distances a', b', c' and d' for defining an object measuring region including the image 11' (FIG. 15) of a standard block for calibration, such as an aluminum step wedge, and values for the distances a, b, c and d for defining the object measuring region including the image of the second metacarpal bone of the right hand.

Furthermore, if necessary, the automatic image read unit may be such as capable of entering values for the distances a, b, c and d for defining one object measuring region or each of a plurality of object measuring regions, capable of sequentially reading images formed in the plurality of object measuring regions, and capable of storing the data of the images respectively in combination with the positions of the corresponding object measuring regions.

The bone-morphometric apparatus in this embodiment requires image storage means comprising a very small number of image memories, is capable of reading images in a very short image read time and, if necessary, is able to read selectively the images formed in a plurality of object measuring regions.

Requiring only a small number of image memories, the bone-morphometric apparatus in this embodiment can be easily formed in a compact construction suitable for carrying and is capable of rapid bone morphometry.

A bone-morphometric apparatus in a further embodiment according to the present invention will be described hereinafter. This bone-morphometric apparatus is capable of surely and efficiently reading roentgenographic images including that of a sample bone formed on an X-ray film regardless of the positional variation of those roentgenographic images.

The bone-morphometric apparatus in this embodiment has the configuration shown in FIGS. 1 and 3 as the basic configuration and comprises coarse image-read means for coarsely reading images including those of the standard matter and a sample bone formed in a wide object measuring region while the film is being fed by the film feed means of the automatic image read unit, to obtain data of picture elements in a thin distribution, picture display means for displaying a coarse picture represented by the data obtained by the coarse image-read means, object measuring region specifying means for specifying narrow object measuring regions respectively including the respective small portions of the images of the standard matter and the sample bone in the coarse picture displayed by the picture display means, and minute image-read means for minutely reading the respective small portions of the images included respectively in the narrow object measuring regions specified by the object measuring region specifying means while the film is being fed by the film feed means, to obtain data of picture elements in a dense distribution.

The coarse image-read means in this embodiment reads the picture elements distributed in a thin distribution in the entire area of the film including the respective images of the standard matter and the sample bone by the linear image read unit while the film is fed at a coarse-feed speed higher than a minute-feed speed for feeding the film for minute reading. Preferably, the coarse-feed speed for coarse reading is two to sixteen times the minute-feed speed for minute reading. When the coarse-feed speed is eight times the minute-feed speed, the number of data obtained by the coarse reading is as small as ⅛ that of data obtained by the minute reading. Thus, the images in the entire wide region can be represented by a small number of image data, so that only a small storage area may be assigned to those image data.

Figure 17:
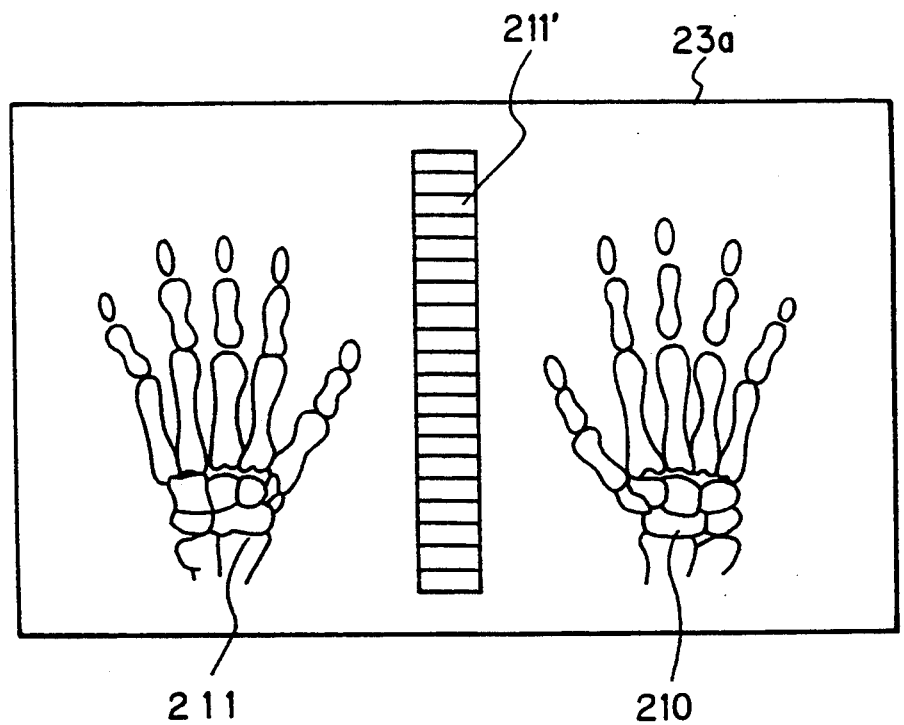
FIG. 17 is a typical plan view showing the roentgenographic images of a sample bone and an aluminum standard step wedge displayed on a display unit for rough image reading.

As shown in FIG. 17, the picture display means displays the picture of the entire wide region represented by the image data obtained by the coarse image-read means. The CRT 23 shown in FIG. 3 is a preferable picture display means. In FIG. 17, the coarse picture 211' of an aluminum step wedge, i.e., the standard matter, the coarse picture of 210 of the bones of the right hand and the coarse picture 211 of the bones of the left hand obtained through coarse image-reading and displayed on the screen 23a of the CRT 23.

Preferably, the display means is able to display the images in a degree of coarseness with respect to a direction perpendicular to the film feed direction substantially the same as the degree of coarseness with respect to the film feed direction to display the images without distortion. Preferably, the distribution of the image data with respect to a direction perpendicular to the image feed direction is thinned by software which regularly omits part of the coarse image data stored in the image storage means in displaying the coarse image data.

The enhancement of the film feed speed for coarse image-reading can simply be achieved by adding software to or modifying the software of the motor control means. The enhancement of the film feed speed reduced image read time.

The object measuring region specifying means in this embodiment specifies narrow object measuring regions respectively including specified portions of the coarse images in the coarse picture displayed on the coarse picture display means. Although the narrow object measuring regions may be specified by any suitable method, a method using the cursor on a CRT is desirable. For example, a narrow object measuring region 213 including part of the image of the aluminum step wedge, i.e., the standard block, and a narrow object measuring region 212 including part of the image 214 of the second metacarpal bone of the right hand are specified as shown in FIG. 18.

Figure 18:
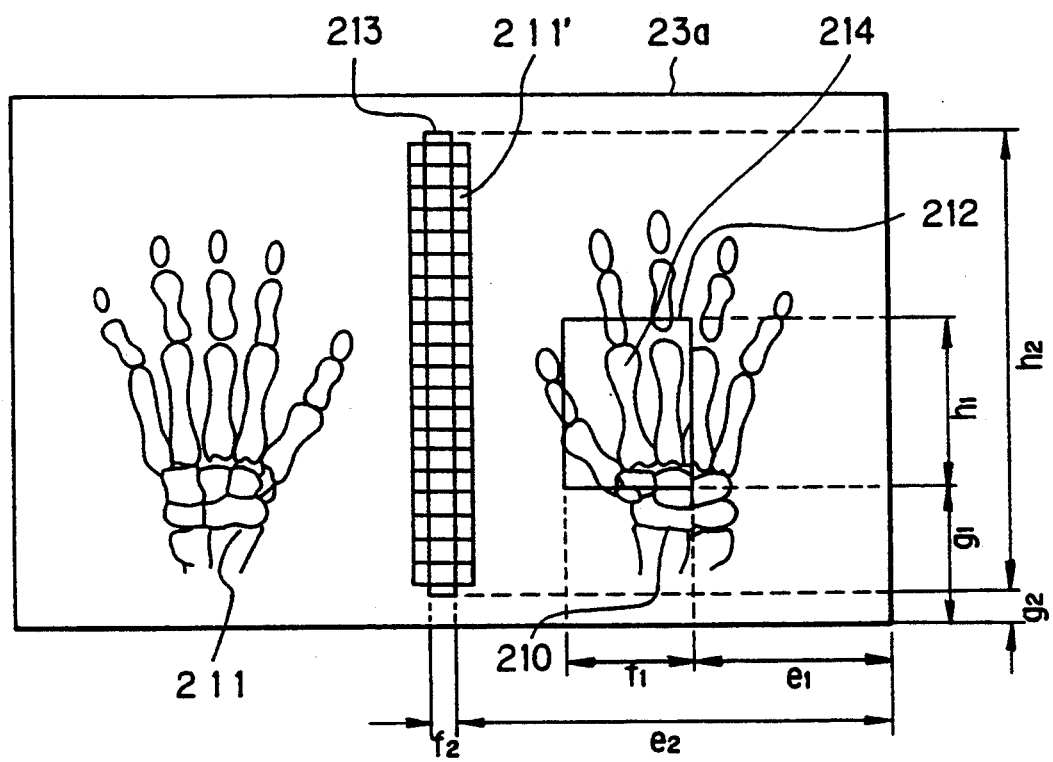
FIG. 18 is a typical plan view, similar to FIG. 17, in which a narrow region is specified by region specifying means.

Concretely, as shown in FIG. 18, the object measuring region 212 is specified by distances $e_1$ and $g_1$ respectively from the right-hand edge and lower side edge of the screen and lengths $f_1$ and $h_1$, and the object measuring region 213 is specified by distances $e_2$ and $g_2$ respectively from the right-hand edge and lower side edge of the screen and lengths $f_2$ and $h_2$ by shifting the cursor. The length $f_2$ for specifying the object measuring region 213 in the image 211' of the aluminum step wedge may be very small to specify an object measuring region like a single thin line. The minute image-read means in this embodiment reads the portions of the images in the narrow object measuring regions specified by the object measuring region specifying means for minute image-reading in a high accuracy by the automatic image read unit while the film is being fed. It is desirable to feed the film at a film feed speed lower than a film feed speed for coarse image-reading to obtain image data of dense picture element distribution with respect to the film feed direction. Furthermore, the minute image-read means is provided desirably with conversion means for converting the specified object measuring region into a film feed distance and a read range with respect to a direction perpendicular to the film feed direction for efficient, minute image-reading. For example, the distances $e_1$, $g_1$, $e_2$ and $g_2$ and the lengths $f_1$, $h_1$, $f_2$ and $h_2$ shown in FIG. 18 are converted by the conversion means; the distance $e_1$ and the length $f_1$ of the object measuring region 212 are converted into corresponding film feed distances, the distance $g_1$ and the length $h_1$ of the object measuring region 212 are converted into corresponding ranges with respect to a direction perpendicular to the film feed direction, the distance $e_2$ and the length $f_2$ of the object measuring region 213 are converted into corresponding film feed distances and the distance $g_2$ and $h_2$ of the object measuring region 213 are converted into corresponding ranges with respect to a direction perpendicular to the film feed direction. Preferably, the film is moved for minute image-reading in a direction reverse to the film feed direction for coarse image-reading, the film is moved at the lower film feed speed only while the minute image-read means travels relative to the film through the lengths $f_1$ and $f_2$, and the image read means functions only in the specified object measuring regions for minute image-reading. That is, the image read means functions for minute image-reading only for the range $h_1$ while the same travels relative to the film through the distance $f_1$ and only for the range $h_2$ while the same travels through the distance $f_2$.

Such an image reading mode of the minute image-read means ensures and facilitates the accurate reading of portions of the respective images of the standard block and the sample bone which are essential to bone morphometry.

During the minute image-reading operation, the stepping motor of the film feed means is controlled so as to feed the film at the higher film feed speed while the automatic image read unit travels relative to the film through regions other than those corresponding to the lengths $f_1$ and $f_2$ to carry out the minute image-reading operation efficiently.

Thus, the stepping frequency of the stepping motor is reduced for minute image-reading operation to read the images formed on the X-ray film by controlling the pulse signal applied to the stepping motor so that the X-ray film is fed intermittently by a distance corresponding to the pitch of the scanning lines at a time. When reading the portion of the image included in the object measuring region 212, the number of the picture elements in a range with respect to the direction of extension of the linear image detector 42 corresponding to the length $h_1$ is counted by a picture element counter and the data of only the picture elements in the range is read and stored in, for example, an image memory. The portion of the image in the object measuring region 213 is read likewise.

The bone-morphometric apparatus in this embodiment is featured by the employment of the means having such image reading functions as the automatic image read means.

The image data obtained through the minute image-reading operation, representing the quantities of transmitted light transmitted through the detected positions on the image of the sample bone, is converted into digital signals representing the respective thicknesses of the steps of the aluminum step wedge corresponding to the respective densities at detected positions on the image to obtain digital data. The data representing the quantities of transmitted light transmitted through the respective images of the sample bone and the aluminum step wedge may be used without converting the same into digital signals. The digital data is stored in suitable storage means, such as the image memory 56 shown in FIG. 3. The bone-morphometric data processing unit 32 processes the stored digital data in the foregoing manner for bone morphometry. The results of the bone-morphometric data processing operation are provided by the output means, such as the printer 25.

The bone-morphometric apparatus in this embodiment is capable of surely and rapidly carrying out the image reading operation and capable of achieving accurate bone morphometry without increasing the storage area with X-ray films having the images of sample bones at different positions.

A bone-morphometric method and a bone-morphometric apparatus having the configuration shown in FIGS. 1 and 3 in further preferred embodiments according to the present invention will be described hereinafter. This bone-morphometric method and this bone-morphometric apparatus incorporates improvements for solving problems that a dark portion of a roentgenographic image cannot be measured precisely and the accurate data of the same cannot be obtained due to leakage in the linear image detector comprising CCDs, when an electric signal representing the quantity of transmitted light transmitted through a light portion contiguous with the dark portion is large.

Prior to the bone morphometry of a sample bone using the quantity of light transmitted through an X-ray film carrying the respective images of the sample bone and a standard matter having varying thickness, a predetermined small quantity $L_0$ of light is applied to a portion of the image of the standard matter corresponding to the vicinity of the edge of the thickest end of the standard matter and the quantity of transmitted light transmitted through the same portion is measured to detect a portion of the image of the standard matter corresponding to the edge of the thickest end of the standard matter, a predetermined quantity L of light greater than the quantity $L_0$ is applied to the image of the standard matter to determine the relation between the thickness of the standard matter and the gradation of the image on the basis of the relation between the quantity of transmitted light and the distance from the edge of the thickest end of the standard matter.

When detecting the portion of the image corresponding to the edge of the thickest end of the standard matter, such as an aluminum step wedge or an aluminum slope, by the morphometric method in this embodiment, the quantity $L_0$ of light smaller than the quantity L of light to be applied to the film in reading the respective images of the standard matter and the sample bone is applied to the vicinity of the portion of the image of the standard matter corresponding to the vicinity of the edge of the thickest end of the standard matter to read the image of the edge of the thickest end of the standard matter.

The quantity $L_0$ of light is set, for example, by directly illuminating the linear image detector 42 comprising CCDs by the light emitted by the linear light source 41 and adjusting the duration of on-state of the linear light source 41 so that the quantity of light received by the linear image detector 42 is in the range of 90 to 95% of the saturation level of the CCDs.

The quantity L of light may be set by the foregoing illuminating light quantity adjusting means capable of adjusting the quantity of illuminating light according to the condition of the images formed on the X-ray film so that accurate bone morphometry can be achieved.

Preferably, a portion of the image of the standard block, i.e., the aluminum step wedge, corresponding to the edge of the thickest end of the standard block is detected, because a portion of the image of the standard block corresponding to the edge of the thinnest end of the standard block, in many cases, is not clear and hence the latter portion is difficult to detect accurately. For example, in the image 311' of the aluminum step wedge shown in FIG. 19, the lower end corresponds to the thickest end of the aluminum step wedge and is the lightest when illuminated.

Figure 19:
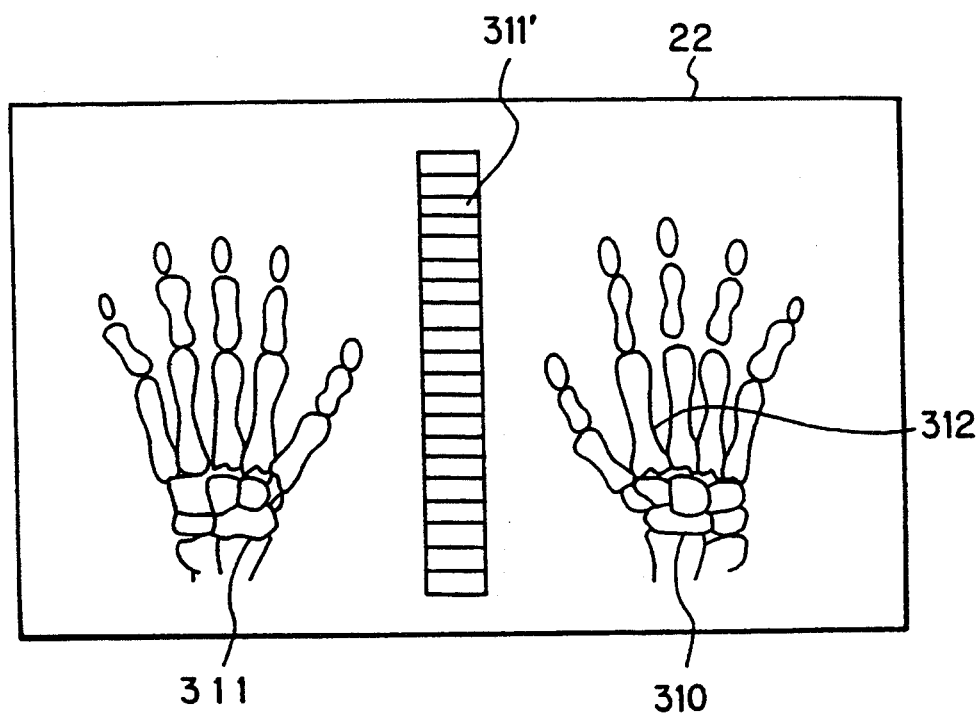
FIG. 19 is a typical plan view of a roentgenogram having the roentgenographic images of a sample bone and an aluminum standard step wedge, for the detection of the end of the aluminum standard step wedge.
Figure 20A:
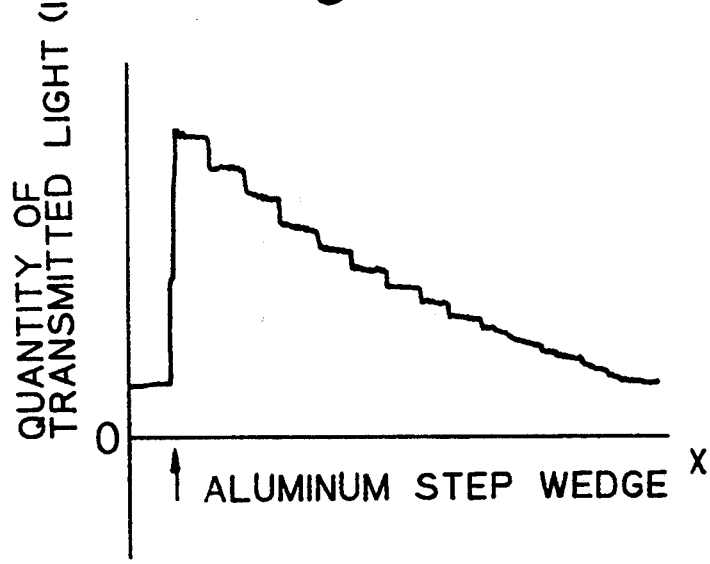
FIGS. 20A and 20B are graphs typically showing patterns for detecting a portion of a roentgenographic image corresponding to an end of an aluminum standard step wedge.
Figure 20B:
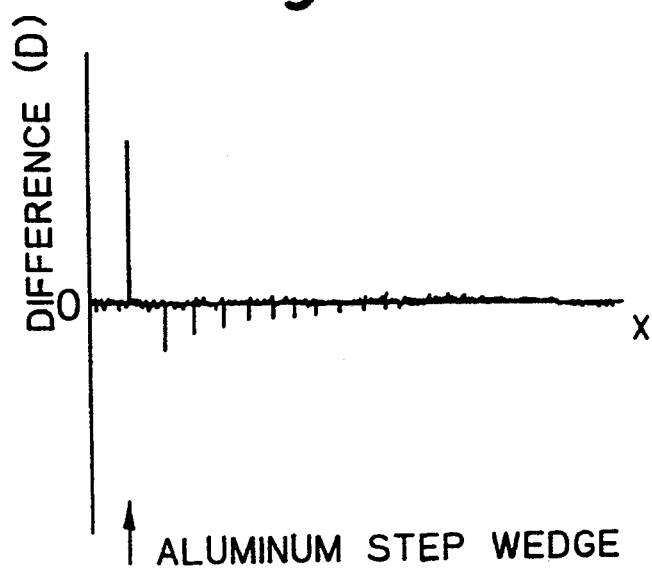

For example, in the image 311' of the aluminum step wedge shown in FIG. 19, suppose that the x-axis is the longitudinal center line of the image 311', the x-axis intersects the lower side edge of the film 22 at a point O, and positive values for x, i.e., distance from the point O, are measured upward on the x-axis. Then, the relationship between the quantity I of transmitted light and the distance x from the point O can typically be represented by the stepped curve as shown in FIG. 20A. The unit for x corresponds to one 63.5 μm wide picture element. The relation between I and x is stored in a storage means, such as the RAM 62, and the mean transmitted light quantity $\bar{I}(x)$ per $\alpha$ is calculated for each value of x by the MPU 60. Preferably, $\alpha$ is five to ten picture elements; for example, seven picture elements. Then, the difference $D = \bar{I}(x+\beta) - \bar{I}(x)$ is calculated for each x. Desirably, $\beta$ is in the range of ten to twenty picture elements, for example, fourteen picture elements, to reduce the influence of noise. FIG. 20B shows a typical relationship between D and x. A position on the image 311' corresponding to a value of x for the maximum value of D corresponds to the edge of the thickest end of the aluminum step wedge. A usual aluminum step wedge has twenty steps 10 mm in width and a 1 mm common thickness difference including the thinnest step 1 mm thick and the thickest step 20 mm thick, and a length of 200 mm.

Thus, this embodiment is able to detect the edge of a portion of the image of the aluminum step wedge corresponding to the edge of the thickest step. Furthermore, the bone-morphometric method is capable of accurately determining the relationship between the thickness of the aluminum step wedge and the quantity of transmitted light transmitted through the aluminum step wedge through the measurement of the quantity of transmitted light along the x-axis by applying the quantity L of illuminating light greater than the quantity $L_0$ of illuminating light to the image of the aluminum step wedge. The quantity L of illuminating light is applied to the image of the sample bone and the quantity of transmitted light transmitted through the image of the sample bone is measured, and then the quantity of transmitted light is converted into the corresponding thicknesses of the steps of the aluminum step wedge with reference to the known relation between the quantity of transmitted light and the thickness of the steps of the aluminum step wedge for further accurate bone morphometry.

The bone-morphometric apparatus in this embodiment is capable of carrying out the foregoing bone-morphometric method and is featured by image read means comprising means for detecting the edge of the image of a standard matter corresponding to the edge of the standard matter while the smaller quantity $L_0$ of illuminating light is applied to the image of the standard matter, and means for reading the respective images of the standard matter and the sample bone while the larger quantity L of illuminating light is applied to the images. The quantity of illuminating light may be controlled, for example, by a lighting frequency control circuit for controlling the lighting frequency, hence the lighting duration, of the light source, such as a LED.

The image storage means of the bone-morphometric apparatus embodying the present invention may be any storage means capable of storing digital signals obtained by converting the quantity of transmitted light transmitted through the roentgenographic image of the sample bone in combination with corresponding positions on the X-ray film. The image memory 56 shown in FIG. 3 is an exemplary image storage means.

The functions of the means for detecting the edge by using the quantity $L_0$ of illuminating light and the means for reading the image by using the quantity L of illuminating light may be executed by the linear light source 41 and linear image detector 42 of the automatic image read unit 31 shown in FIG. 3. The functions of the lighting frequency control circuit may be executed by the light source control circuit 45.

After storing the data of the roentgenographic image of the sample bone in the image memory 56, the stored data can be readily processed by the bone-morphometric data processing unit 32. The bone-morphometric method or bone-morphometric apparatus in this embodiment is capable of surely and accurately reading the image of the standard block, i.e., the aluminum step wedge, for further accurate bone morphometry.

A morphometric bone assay system in a preferred embodiment according to the present invention will be described hereinafter. The morphometric bone assay system comprises the aforesaid bone-morphometric apparatus for the bone morphometry of a sample bone, first transmission means for transmitting bone-morphometric data obtained by the bone-morphometric apparatus, a morphometric bone assay apparatus which stores the bone-morphometric data transmitted by the transmission means and assays the sample bone by using the stored bone-morphometric data, bone-morphometric data obtained in the past and, if necessary, other data, and second transmission means for transmitting the results of the morphometric bone assay of the sample bone to the bone-morphometric apparatus.

The bone-morphometric apparatus is such an apparatus as shown in FIG. 3 which processes images formed by transmitted light transmitted through the respective roentgenographic images of a standard block and a sample bone formed on an X-ray film or an apparatus as shown in FIG. 8 which processes the respective radiographic images of a standard block and a sample bone obtained by irradiating the standard block and the sample bone with radioactive rays, such as X-rays or gamma rays.

The morphometric bone assay apparatus comprises storage means for storing bone-morphometric data transmitted thereto by the communication means, and assay means for assaying the data of the sample bone including the quantity of bone mineral through the analysis of the bone-morphometric data given thereto in combination with bone-morphometric data previously stored therein.

If possible, various bone-morphometric information may be included in the assay. Concretely, the assay of the time-dependent variation of the sample bone based on the examination of the previous bone-morphometric data, and the analysis of the difference between the present bone-morphometric data and the last bone-morphometric data. The morphometric bone assay system may be provided with functions for storing morphometric indices of bones of healthy persons of the same sex and the same age as reference indices and for comparing the morphometric indices of the sample bone with those reference indices. Records of medication for therapy may be stored for use in combination with the morphometric data for morphometric bone assay.

Figure 21:
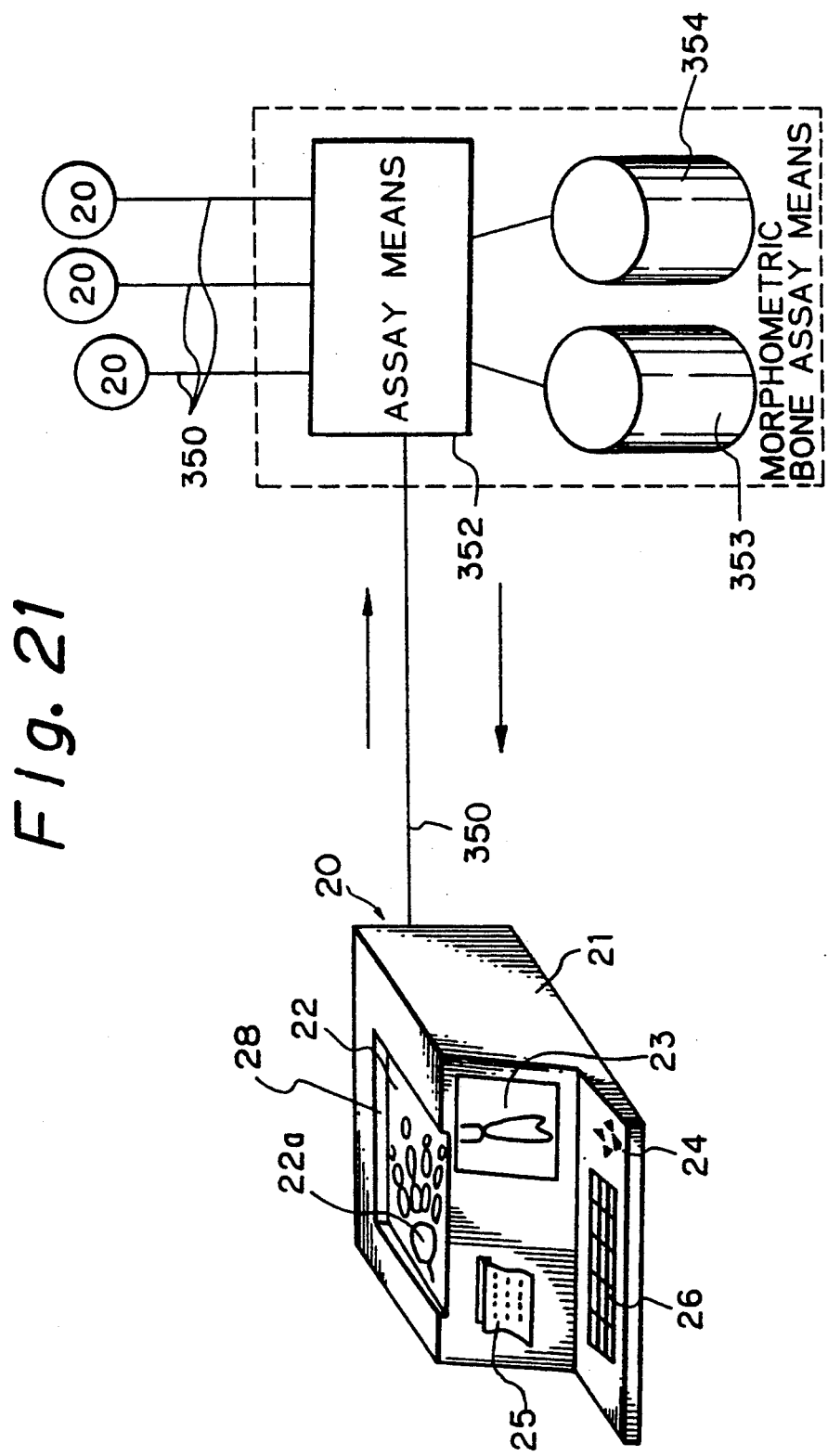
FIG. 21 is a block diagram of a morphometric bone assay system in a preferred embodiment according to the present invention, comprising a bone-morphometric apparatus using an X-ray film, and a morphometric bone assay apparatus connected to the bone-morphometric apparatus.

FIG. 21 is a block diagram of a morphometric bone assay system including a bone-morphometric apparatus which uses roentgenograms. Naturally, the bone-morphometric apparatus may be substituted by the radiographic bone-morphometric apparatus shown in FIG. 8.

Referring to FIG. 21, the morphometric bone assay system comprises a morphometric bone assay apparatus 351, and one or a plurality of bone-morphometric apparatus 20 connected by communication means 350 including first and second transmission means, such as telephone circuits. The morphometric bone assay apparatus 351 comprises storage means 353 and 354, and assay means 352. Preferably, the morphometric bone assay apparatus 351 is provided with self-diagnostic means to check the operating condition of the bone-morphometric apparatus 20.

The self-diagnostic means checks the condition of inputs, such as the condition of the received image data of a sample bone, in order to ascertain that the condition is satisfactory, and maintains the normal functions of the morphometric bone assay apparatus by inquiring and eliminating the causes of malfunction to ensure the correct bone morphometry of the sample bone.

In the case of the practical self-diagnosis of the bone-morphometric apparatus 20 which uses an X-ray film 22 carrying the roentgenogram of a sample bone, a central equipment compares periodically the respective output levels of the light source and the linear image detector 42 with reference levels, respectively, to determine the secular degradation of the light source and the linear image detector 42. It is desirable to readjust the associated apparatus when the degradation has proceeded beyond a given limit.

The morphometric bone assay apparatus 351 may be provided with generally known means for inquiring the causes of malfunction including (1) means for checking the contents of the data memory (RAM 62) and image memory (image memory 56) of the computer by using check sums, (2) means for testing the functions of the printer, the CRT controller 64 and the keyboard 26, (3) means for testing the operation of the motor controller by using a standard test film for testing film feed and (4) means for luminance regulation test for checking the functions of the image read unit 31 and correcting function.

It is desirable to realize the self-diagnostic functions on the assumption that variation in the quantity of light with respect to the direction of the width of the linear image detector is corrected for every measurement of the roentgenogram, the basic functions of the computer and communication functions are checked through selftests without using the communication means and the basic functions of the computer and the communication functions are normal.

When telephone circuits are employed as the communication means 350, practically, MODEM communication using public telephone circuits or use of a leased circuit is preferable. Accordingly, the bone-morphometric data processing unit 32 of the bone-morphometric apparatus 20 is provided with a MODEM 67.

Thus, the present invention enables the use of practically and economically advantageous telephone circuits by transmitting a small amount of simplified data, such as the results of morphometric bone assay performed by the morphometric bone assay apparatus and the results of bone morphometry performed by the bone-morphometric apparatus, even if a large amount of bone-morphometric data of sample bones is produced.

The bone-morphometric apparatus 20 of the morphometric bone assay system of the present invention are installed respectively at the sites of roentgenographic operation for the quick bone morphometry immediately after X-raying sample bones, transmits the simplified results of bone morphometry to the morphometric bone assay apparatus 351, performs collectively the complicated assay of sample bones including the comparison of the simplified results with stored bone-morphometric data by the morphometric bone assay apparatus 351, and feeds back the results of morphometric bone assay immediately.

The contents of communication between each bone-morphometric apparatus 20 and the morphometric bone assay apparatus 351 are, for example, (1) information about the examinee including an ID number identifying the examinee, name, data of birth, date of initial registration, the diagnosis, the newest bone-morphometric data and data storage location, (2) the bone-morphometric data of the examinee including data number, date of X-raying, measuring illuminance and Σ GS, and (3) system data including the number of all the registered examinee, the number of the bone-morphometric apparatus, the title of the installation and the results of the self-diagnosis of the apparatus.

The morphometric bone assay system thus constructed carries out morphometric bone assay at a location far apart from the bone-morphometric apparatus 20 and feeds back the results of morphometric bone assay to enable quick bone morphometry and bone morphometry. Furthermore the morphometric bone assay system enables the use of the bone-morphometric apparatus at remote places and ensures accurate bone morphometry.

Furthermore, the morphometric bone assay system in accordance with the present invention is able to use existing telephone circuits as communication means realizes collective and efficient bone morphometry by the plurality of bone-morphometric apparatus distributed as terminal equipments in different regions and the single morphometric bone assay apparatus as the central equipment. The morphometric bone assay system carries out automatic morphometric bone assay quickly and efficiently through the automatic bone morphometry including the automatic reading of the roentgenograms or radiograms of sample bones.

We claim:

1. A bone-morphometric apparatus comprising, in combination:

automatic image read means for automatically reading the bone-morphometric data of the image of a sample bone formed on an X-ray film by irradiating the sample bone together with a given standard matter with X-rays, through the illumination of the image and the detection of the quantity of light transmitted through the image wherein said automatic image read means comprises automatic film feed means for feeding the X-ray film; linear light source means for emitting light to illuminate the X-ray film; and linear image detecting means for detecting the quantity of transmitted light transmitted through the X-ray film;

image storage means for storing the bone-morphometric data of the image of the sample bone obtained by the automatic image read means;

arithmetic means for processing the bone-morphometric data of the image stored in the image storage means for bone morphometry; and bone-morphometric data output means for providing the results of bone morphometry obtained through the operation of the arithmetic means.

2. A bone-morphometric apparatus according to claim 1 further comprising:

picture display means for displaying a picture corresponding to the image of the sample bone represented by the bone-morphometric data obtained by said automatic image read means; and point input means for entering points to specify reference positions necessary for bone morphometry on the picture of the sample bone displayed on the picture display means.

3. A bone-morphometric apparatus according to claim 2 further comprising case means provided in its front surface with the screen of said picture display means.

4. A bone-morphometric apparatus according to claim 2, wherein said point input means is capable of erasing the points specifying the reference positions necessary for bone morphometry on the picture of the sample bone as well as entering the points.

5. A bone-morphometric apparatus according to claim 2, wherein said point input means comprises mark display means for displaying predetermined marks representing the points on said picture display means in predetermined pictures contrastive to the background, and the mark display means reverses the respective densities of portions for forming the marks in the screen of said picture display means to display the marks contrastive to the background.

6. A bone-morphometric apparatus according to claim 1, wherein the automatic film feed means of said automatic image read means is provided with film feed control means for feeding the X-ray film to recognize the image of the predetermined standard matter and performs control functions so that the image is illuminated by the light emitted by said light source means, and the light source means of said automatic image read means is provided with illuminating light quantity adjusting means for adjusting the quantity of illuminating light so that the quantity of light transmitted through a given portion of the standard matter is in a given light quantity range.

7. A bone-morphometric apparatus according to claim 6, wherein said film feed control means is intermittent feed control means including a stepping motor, and capable of controlling the stepping motor so that the X-ray film is fed intermittently at a fixed rate.

8. A bone-morphometric apparatus comprising, in combination:

automatic image read means for automatically reading the bone-morphometric data of the image of a sample bone formed on an X-ray film by irradiating the sample bone together with a given standard matter with X-rays, through the illumination of the image and the detection of the quantity of light transmitted through the image wherein said automatic image read means comprises:

light source means for emitting light for illuminating the X-ray film;

image detecting means for detecting the quantity of transmitted light transmitted through the X-ray film;

region search means for searching the image of the given standard matter for a region that transmits a quantity of light meeting predetermined conditions;

first decision means for making a decision as to whether or not a range of the quantity of transmitted light for an object measuring region for bone morphometry is included in the range of the quantity of transmitted light for the region in the image of the standard matter;

second decision means for making a decision as to whether or not the quantity of light transmitted through the object measuring region and the quantity of light transmitted through the standard matter meet a given resolution; and illuminating light adjusting means for adjusting the quantity of light to be emitted by said light source means on the basis of the decision made by the first decision means;

image storage means for storing the bone-morphometric data of the image of the sample bone obtained by the automatic image read means;

arithmetic means for processing the bone-morphometric data of the image stored in the image storage means for bone morphometry; and bone-morphometric data output means for providing the results of bone morphometry obtained through the operation of the arithmetic means.

9. A bone-morphometric apparatus according to claim 8, wherein said light source means comprises:

first means for obtaining the quantity I of transmitted light transmitted through a portion of the standard matter, greater than and nearly the same as the maximum quantity of light transmitted through said object measuring region when increasing the quantity of illuminating light to be emitted;

second means for adjusting the quantity of illuminating light to be emitted so that the quantity I of transmitted light approaches a given maximum quantity $I_{max}$;

third means for searching the object measuring region for an area which transmits a quantity of transmitted light exceeding the given quantity $I_{max}$ in reducing the quantity of illuminating light to be emitted; and fourth means for adjusting the quantity of illuminating light to be emitted on the basis of an appropriate quantity of illuminating light estimated taking into consideration the size of the area.

10. A bone-morphometric apparatus according to claim 8, wherein said automatic image read means includes an automatic film feed means for feeding the X-ray film, and said bone-morphometric apparatus comprises:

picture display means for displaying a picture corresponding to the image of the sample bone represented by the bone-morphometric data obtained by said automatic image read means;

point input means for entering points to specify reference positions on the picture of the sample bone displayed on the picture display means;

storage means for storing the points specifying the reference positions; and another point input means for specifying new points on the basis of the points specifying the reference positions, stored in the storage means when the image of the standard matter and the object measuring region in the image of the sample bone are read automatically by said automatic image read means by using an adjusted quantity of illuminating light in performing again the bone morphometry of the image of the sample bone after adjusting the quantity of illuminating light.

11. A bone-morphometric apparatus comprising, in combination:

automatic image read means for automatically reading the bone-morphometric data of the image of a sample bone formed on an X-ray film by irradiating the sample bone together with a given standard matter with X-rays, through the illumination of the image and the detection of the quantity of light transmitted through the image wherein said automatic image read means comprises:

automatic film feed means for automatically feeding the X-ray film;

linear light source means extended perpendicularly to a film feed direction in which the X-ray film is fed, to emit illuminating light for illuminating the X-ray film;

linear image detecting means for detecting the quantity of transmitted light transmitted through the X-ray film; and image read region setting means for setting a distance a from a reference position with respect to the film feed direction for the skipping feed of the X-ray film, a distance b for the image reading feed of the X-ray film, on the extension of the distance a, a distance c from a reference position with respect to a direction perpendicular to the film feed direction along the direction perpendicular to the film feed direction and an image scanning distance d on the extension of the distance c;

image storage means for storing the bone-morphometric data of the image of the sample bone obtained by the automatic image read means;

arithmetic means for processing the bone-morphometric data of the image stored in the image storage means for bone morphometry; and bone-morphometric data output means for providing the results of bone morphometry obtained through the operation of the arithmetic means.

12. A bone-morphometric apparatus according to claim 11, wherein said automatic film feed means comprises:

feed roller means disposed so as to nip the X-ray film;

a stepping motor for driving the feed roller means;

pulse signal control means for controlling a pulse signal for driving the stepping motor, and converting means for converting the distance a into a corresponding pulse signal for driving the stepping motor for the skipping feed of the X-ray film, converting the distance b into a number of scanning lines for which said linear image detecting means performs image detecting operation, and converting the distances c and d respectively into numbers of detecting elements of said linear image detecting means.

13. A bone-morphometric apparatus according to claim 11, wherein said image read region setting means comprises:

external input means for entering the distances a, b, c and d; and storage means for storing the distances a, b, c and d entered by the external input means.

14. A bone-morphometric apparatus according to claim 11, wherein the X-ray film has two object measuring regions respectively for the standard matter and the sample bone, and an image for calibration, said automatic image read means has object region setting means for setting the distances a, b, c and d for each of the object regions, and said image storage means has image storage means for storing images read from the two object regions.

15. A bone-morphometric apparatus comprising, in combination:

automatic image read means for automatically reading the bone-morphometric data of the image of a sample bone formed on an X-ray film by irradiating the sample bone together with a given standard matter with X-rays, through the illumination of the image and the detection of the quantity of light transmitted through the image; wherein said automatic image read means comprises:

automatic film feed means for automatically feeding the X-ray film;

linear light source means extended perpendicularly to a film feed direction in which the X-ray film is fed, to emit illuminating light for illuminating the X-ray film;

linear image detecting means for detecting the quantity of transmitted light transmitted through the X-ray film;

coarse image-read means for coarsely reading images including those of the standard matter and the sample bone formed in a wide object measuring region to obtain the data of picture elements in a coarse distribution while the X-ray film is being fed by the automatic film feed means;

display means for displaying a coarse picture represented by the data obtained by the coarse image-read means;

object measuring region specifying means for specifying narrow object measuring regions respectively including the respective small portions of the images of the standard matter and the sample bone in the coarse picture displayed by the display means; and minute image-read means for reading portions of the images of the standard matter and the sample bone in the narrow object measuring regions specified by the object measuring region specifying means in a dense picture element distribution by said image detecting means while the X-ray film is being fed by said automatic film feed means;

image storage means for storing the bone-morphometric data of the image of the sample bone obtained by the automatic image read means;

arithmetic means for processing the bone-morphometric data of the image stored in the image storage means for bone morphometry; and bone-morphometric data output means for providing the results of bone morphometry obtained through the operation of the arithmetic means.

16. A bone-morphometric apparatus according to claim 15, wherein said coarse image-read means reads the data of picture elements in a thin distribution with respect to the film feed direction while the X-ray film is being fed at a higher feed speed by said automatic film feed means.

17. A bone-morphometric apparatus according to claim 16, wherein said display means for displaying the coarse picture expressed by the data of the picture elements obtained by coarse image-reading displays the picture in a degree of coarseness with respect to a direction perpendicular to the film feed direction substantially the same as the degree of coarseness with respect to the film feed direction.

18. A bone-morphometric apparatus according to claim 17, wherein said object measuring region specifying means specifies the narrow regions including the portions of the pictures of the standard matter and the sample bone by locating a cursor on the pictures displayed on the display means for displaying the coarse picture.

19. A bone-morphometric apparatus according to claim 15 further comprising data converting means for converting the narrow object measuring regions specified by said object measuring region specifying means into data representing film feed distances and read ranges with respect to a direction perpendicular to the film feed direction to make said minute image-read means operate for the minute image-reading of the data of picture elements distributed in a dense distribution in the specified narrow object measuring regions on the basis of data provided by the data converting means.

20. A bone-morphometric apparatus comprising, in combination:

automatic image read means for automatically reading the bone-morphometric data of the image of a sample bone formed on an X-ray film by irradiating the sample bone together with a given standard matter with X-rays, through the illumination of the image and the detection of the quantity of light transmitted through the image wherein said automatic image read means comprises:

light source means for emitting light to illuminate the X-ray film;

image detecting means for detecting the quantity of transmitted light transmitted through the X-ray film;

light quantity control means for controlling the quantity of illuminating light for illuminating the X-ray film;

detecting means for detecting a portion of the image of the standard matter corresponding to the thicker end of the standard matter by measuring the quantity of light transmitted through a portion of the image of the standard matter corresponding to the vicinity of the thickest end of the standard matter, during the application of a given smaller quantity of $L_0$ of illuminating light to the same portion of the image corresponding to the vicinity of the thickest end of the standard matter; and measuring means for measuring the quantity of transmitted light transmitted through the image of the standard matter formed on the X-ray film, during the application of a given larger quantity L of illuminating light to the image of the standard matter, to determine the relation between the quantity of transmitted light and the distance from the thicker end of the image of the standard matter;

image storage means for storing the bone-morphometric data of the image of the sample bone obtained by the automatic image read means;

arithmetic means for processing the bone-morphometric data of the image stored in the image storage means for bone morphometry; and bone-morphometric data output means for providing the results of bone morphometry obtained through the operation of arithmetic means.

21. A bone-morphometric apparatus according to claim 1, wherein said arithmetic means comprises:

first smoothing means for obtaining a first smoothed density pattern by initially obtaining a plurality of density patterns of said image of the sample bone formed on said X-ray film, along a plurality of different substantially parallel scanning lines in a predetermined object measuring region of said image of the sample bone from said bone-morphometric data read by said automatic image read means, and by subsequently averaging said plurality of density patterns of said image at predetermined points where said the plurality of different scanning lines cross a line extending longitudinally through said X-ray film image, so as to be substantially perpendicular to said plurality of scanning lines; and pattern data converting means for converting the density data of the first smoothed density pattern into those expressed by the thickness of the standard matter to obtain a converted pattern.

22. A bone-morphometric apparatus according to claim 21, wherein said arithmetic means further comprises a second smoothing means for obtaining a second smoothed density pattern by averaging values of said converted pattern at a plurality of predetermined points on said scanning lines, said second smoothed density pattern being processed for said bone-morphometry of said sample bone.

23. A bone-morphometric apparatus according to claim 21, wherein said pattern data converting means converts the density pattern into a thickness pattern represented by the thickness of the standard matter on the basis of the relation between the thickness of the standard matter and the quantity of transmitted light determined by measuring the quantity of light transmitted through the image of the standard matter formed on the X-ray film.

24. A morphometric bone assay system comprising:
a bone-morphometric apparatus for the bone morphometric sample bone;

first transmission means for transmitting bone-morphometric data obtained by the bone morphometry of the sample bone as output data;

morphometric bone assay means for storing the bone-morphometric data transmitted by the first transmission means thereto and for performing the morphometric bone assay of the sample bone by using the stored bone-morphometric data in combination with corresponding previously stored bone-morphometric data and, if need be, other stored data; and second transmission means for transmitting the results of the morphometric bone assay of the sample bone provided by the morphometric bone assay means to the bone-morphometric apparatus;

wherein said bone-morphometric apparatus is provided with self-diagnostic means for diagnosing its own operating condition.

25. A morphometric bone assay system according to claim 24, wherein said first and second transmission means utilize telephone circuits.

26. A morphometric bone assay system according to claim 24, wherein said morphometric bone assay means is a single morphometric bone assay apparatus, and a plurality of bone-morphometric apparatus like said bone-morphometric apparatus are connected through said first and second transmission means to the morphometric bone assay apparatus.

27. A morphometric bone assay system according to claim 24, wherein said bone-morphometric apparatus comprises:

automatic image read means for automatically reading the bone-morphometric data of the image of a sample bone formed on an X-ray film by irradiating the sample bone together with a given standard matter with X-rays, through the illumination of the image and the detection of the quantity of transmitted light transmitted through the image;

image storage means for storing the bone-morphometric data of the image of the sample bone obtained by the automatic image read means;

arithmetic means for processing the bone-morphometric data of the image stored in the image storage means for bone morphometry; and bone-morphometric data output means for providing the results of bone morphometry obtained through the operation of the arithmetic means.

28. A morphometric bone assay system according to claim 24, wherein said bone-morphometric apparatus comprises:

image storage means for storing the radiographic image of the sample bone formed by irradiating the sample bone with radioactive rays and recording the radioactive rays transmitted through the sample bone;

arithmetic means for processing image data representing the radiographic image of the sample bone for bone morphometry; and bone-morphometric data output means for providing the results of the operation of the bone-morphometric data.

29. A bone-morphometric method comprising:
an image reading step of reading a radiographic image of a sample bone formed by irradiating the sample bone with radioactive rays and recording the transmitted radioactive rays transmitted through the sample bone;

a pattern smoothing step of obtaining a first smoothed density pattern by obtaining a plurality of density patterns of said radiographic image recorded with respect to a predetermined object measuring region thereof along a plurality of different scanning lines, and by averaging the plurality of density patterns of said radiographic image at predetermined points where the plurality of substantially parallel scanning lines cross a line extending longitudinally through said radiographic image, so as to be substantially perpendicular to said plurality of scanning lines;

a data converting step of converting the data representing the first smoothed density pattern into those represented by the thickness of a standard matter to obtain a converted density pattern; and an arithmetic step of operating the data representing the converted density pattern for the bone morphometry of the sample bone.

30. A bone-morphometric method according to claim 29, wherein a second smoothed density pattern is obtained by averaging the data of the converted density pattern at a plurality of points in the vicinity of the scanning line, in order to obtain said converted density pattern after the data converting step, and the data of said second smoothed density pattern is used in the arithmetic step.

31. A bone-morphometric method according to claim 29, wherein the image data of the image of the sample bone formed together with that of a given standard matter having varying thickness on an X-ray film is obtained in the image read step by illuminating the image of the sample bone and detecting the quantity of light transmitted through the image of the sample bone, the data of the density pattern is converted into those expressed by the thickness of the standard matter on the basis of the relation between the thickness of the standard matter and the quantity of transmitted light in the data converting step.

32. A bone-morphometric method for bone morphometry of a sample bone, comprising illuminating an X-ray film carrying respective images of a sample bone and a given standard matter having varying thickness formed simultaneously thereon, and using a quantity of light transmitted through a X-ray film, characterized in:

determining a region in the image of the standard matter transmitting a quantity of transmitted light meeting a given condition;

making a first decision as to whether or not the range for the quantity of light transmitted through an object measuring region is included in a range for the quantity of light transmitted through a region in the image of the standard matter determined in the region determining step;

making a second decision as to whether or not the quantity of light transmitted through the object measuring region and the corresponding quantity of light transmitted through the image of the standard matter meet a given resolution; and adjusting the quantity of illuminating light to be applied to the X-ray film according to the second decision.

33. A bone-morphometric method according to claim 32, wherein, a third decision is made on whether or not the gamma value of the object measuring region is greater than a predetermined value, after the second decision.

34. A bone-morphometric method according to claim 32, wherein in increasing the quantity of illuminating light, a quantity I of transmitted light transmitted through the standard matter greater than and nearly equal to the maximum quantity of transmitted light transmitted through the object measuring region is determined, and the quantity of the illuminating light is adjusted so that the quantity I of transmitted light is not greater than and nearly equal to a predetermined value $I_{max}$.

35. A bone-morphometric method according to claim 32, wherein, in reducing the quantity of illuminating light, a portion of the object measuring region transmitting a quantity of transmitted light exceeding the predetermined value $I_{max}$ is detected, an appropriate quantity of illuminating light is estimated taking into consideration the size of the portion, and the quantity of illuminating light is adjusted to the estimated appropriate quantity of illuminating light.

36. A bone-morphometric method for the bone morphometry of a sample bone, comprising illuminating an X-ray film carrying the respective images of a sample bone and a give standard matter having varying matter formed simultaneously thereon, and using a quantity of transmitted light transmitted through the X-ray film, characterized in:

applying a predetermined smaller quantity $L_0$ of illuminating light to a portion of an image of the standard matter corresponding to the vicinity of the thicker end of the standard matter, detecting the quantity of transmitted light transmitted through the portion of the image of the standard matter to detect the thicker end of the image of the standard matter, applying a predetermined larger quantity L of illuminating light greater than the quantity $L_0$ to the image of the standard matter to determine the relationship between the thickness of the standard matter and the gradation of the image of the same on the basis of the relation between the quantity of light transmitted through the image of the standard matter and the distance from the detected end of the same.

* * * * *

UNITED STATES PATENT AND TRADEMARK OFFICE
CERTIFICATE OF CORRECTION

PATENT NO. : 5,365,564
DATED : November 15, 1994
INVENTOR(S) : Yoshida, et al

It is certified that error appears in the above-indentified patent and that said Letters Patent is hereby corrected as shown below:

On the title page: Item [75] should read -- Makoto Yoshida, Kobe --.

Signed and Sealed this

Twenty-sixth Day of September, 1995

Attest:

BRUCE LEHMAN

*Attesting Officer*                *Commissioner of Patents and Trademarks*